(12) United States Patent
Sekowski

(10) Patent No.: US 11,540,703 B2
(45) Date of Patent: Jan. 3, 2023

(54) STEERABLE MICRO-ENDOSCOPE

(71) Applicant: Research Development International Corporation, Pasadena, CA (US)

(72) Inventor: Marek Sekowski, Pacific Palisades, CA (US)

(73) Assignee: RESEARCH DEVELOPMENT INTERNATIONAL CORPORATION, Pasadena, CA (US)

( * ) Notice: Subject to any disclaimer, the term of this patent is extended or adjusted under 35 U.S.C. 154(b) by 1000 days.

(21) Appl. No.: 16/332,762

(22) PCT Filed: Feb. 8, 2016

(86) PCT No.: PCT/US2016/017033
§ 371 (c)(1),
(2) Date: Mar. 12, 2019

(87) PCT Pub. No.: WO2016/171780
PCT Pub. Date: Oct. 27, 2016

(65) Prior Publication Data
US 2021/0290039 A1    Sep. 23, 2021

Related U.S. Application Data

(63) Continuation-in-part of application No. PCT/US2015/027170, filed on Apr. 22, 2015, and a
(Continued)

(51) Int. Cl.
*A61B 1/00* (2006.01)
*A61B 1/005* (2006.01)
(Continued)

(52) U.S. Cl.
CPC .......... *A61B 1/0052* (2013.01); *A61B 1/0055* (2013.01); *A61B 1/0057* (2013.01);
(Continued)

(58) Field of Classification Search
None
See application file for complete search history.

(56) References Cited

U.S. PATENT DOCUMENTS

| 4,398,910 A | 8/1983 | Blake |
| 4,402,685 A | 9/1983 | Buhler |

(Continued)

FOREIGN PATENT DOCUMENTS

| CN | 1861010 A | 11/2006 |
| CN | 102438532 A | 5/2012 |

(Continued)

OTHER PUBLICATIONS

U.S. Appl. No. 15/751,150, Sekowski, filed Feb. 7, 2018.
(Continued)

*Primary Examiner* — Timothy J Neal
(74) *Attorney, Agent, or Firm* — Ladas & Parry, LLP

(57) ABSTRACT

An endoscope comprising: a tubular elongated member; a tensioning wire in a tensioning lumen along one side of the elongated member, between the proximal end and the distal end of the elongated member; a head arranged at the distal end of the elongated member and comprising: a tubular tensioning ring attached to the distal end of the tensioning wire and having a same external diameter as the elongated member; an imaging sensor having a rectangular cross section, arranged at a distal end of the head; and a tubular distal shell arranged longitudinally around the imaging sensor and having an inner diameter identical to or slightly larger than a diagonal of the rectangular cross section of the imaging sensor; wherein a tubular jacket sheathes the elongated member and the tensioning ring of the head.

9 Claims, 13 Drawing Sheets

Related U.S. Application Data continuation-in-part of application No. PCT/US2015/027170, filed on Apr. 22, 2015.

(51) Int. Cl.

| | | |
|---|---|---|
| *G02B 23/24* | (2006.01) | |
| *A61B 1/05* | (2006.01) | |
| *A61B 1/07* | (2006.01) | |
| *A61B 1/018* | (2006.01) | |
| *A61B 18/14* | (2006.01) | |
| *A61B 17/00* | (2006.01) | |

(52) U.S. Cl.
CPC ............... *A61B 1/05* (2013.01); *A61B 1/07* (2013.01); *G02B 23/2476* (2013.01); *A61B 1/00087* (2013.01); *A61B 1/018* (2013.01); *A61B 18/1492* (2013.01); *A61B 2017/00318* (2013.01)

(56) References Cited

U.S. PATENT DOCUMENTS

| | | | |
|---|---|---|---|
| 4,451,256 A | 5/1984 | Weikl | |
| 4,498,902 A | 2/1985 | Ash | |
| 4,566,400 A | 1/1986 | Keenan | |
| 4,569,347 A | 2/1986 | Frisbie | |
| 4,580,551 A | 4/1986 | Siegmund | |
| 4,616,631 A | 10/1986 | Takahashi | |
| 4,718,407 A | 1/1988 | Chikama | |
| 4,742,817 A | 5/1988 | Kawashima | |
| 4,781,690 A | 11/1988 | Ishida | |
| 4,788,967 A | 12/1988 | Ueda | |
| 4,798,193 A | 1/1989 | Giesy | |
| 4,878,485 A * | 11/1989 | Adair | A61B 1/00101 600/122 |
| 4,888,000 A | 12/1989 | McQuilkin | |
| 4,997,424 A | 3/1991 | Little | |
| 5,108,368 A | 4/1992 | Hammerslag | |
| 5,131,407 A | 7/1992 | Ischinger | |
| 5,147,332 A | 9/1992 | Moorehead | |
| 5,195,978 A | 3/1993 | Schiffer | |
| 5,197,457 A | 3/1993 | Adair | |
| 5,213,093 A | 5/1993 | Swindle | |
| 5,299,562 A | 4/1994 | Heckele | |
| 5,324,269 A | 6/1994 | Miraki | |
| 5,325,845 A | 7/1994 | Adair | |
| 5,342,299 A | 8/1994 | Snoke | |
| 5,383,852 A | 1/1995 | Stevens | |
| 5,397,311 A | 3/1995 | Walker | |
| 5,405,334 A | 4/1995 | Roth | |
| 5,423,312 A * | 6/1995 | Siegmund | A61B 1/042 385/133 |
| 5,438,975 A * | 8/1995 | Miyagi | A61B 1/00071 600/109 |
| 5,507,725 A | 4/1996 | Savage | |
| 5,533,986 A | 7/1996 | Mottola | |
| 5,571,085 A | 11/1996 | Accisano | |
| 5,674,182 A | 10/1997 | Suzuki | |
| 5,704,899 A | 1/1998 | Milo | |
| 5,817,072 A | 10/1998 | Lampropoulos | |
| 5,836,306 A | 11/1998 | Duane | |
| 6,030,360 A | 2/2000 | Biggs | |
| 6,083,152 A | 7/2000 | Strong | |
| 6,159,198 A | 12/2000 | Gardeski | |
| 6,171,235 B1 | 1/2001 | Konstorum et al. | |
| 6,193,691 B1 | 2/2001 | Beardsley | |
| 6,497,681 B1 | 12/2002 | Brenner | |
| 6,740,030 B2 | 5/2004 | Martone | |
| 6,887,417 B1 | 5/2005 | Gawreluk | |
| 7,033,317 B2 | 4/2006 | Pruitt | |
| 7,048,719 B1 | 5/2006 | Monetti | |
| 7,658,738 B2 | 2/2010 | Nobis | |
| 8,029,473 B2 | 10/2011 | Carter | |
| 8,262,563 B2 | 9/2012 | Bakos | |
| 8,320,650 B2 | 11/2012 | Demos | |
| 8,517,921 B2 | 8/2013 | Tremaglio | |
| 8,932,208 B2 | 1/2015 | Kendale | |
| 9,468,362 B2 | 10/2016 | Goldfarb | |
| 10,368,910 B2 | 8/2019 | Eversull | |
| 2002/0068912 A1 | 6/2002 | Merdan | |
| 2002/0072712 A1 | 6/2002 | Nool | |
| 2003/0032941 A1 | 2/2003 | Boyle | |
| 2003/0093085 A1 | 5/2003 | Leopold | |
| 2003/0130564 A1 | 7/2003 | Martone | |
| 2003/0130620 A1 | 7/2003 | Alokaili | |
| 2003/0171650 A1 | 9/2003 | Tartaglia | |
| 2003/0187427 A1 | 10/2003 | Gatto | |
| 2003/0212373 A1 | 11/2003 | Hall | |
| 2003/0233024 A1 * | 12/2003 | Ando | A61B 1/00096 600/111 |
| 2003/0233115 A1 | 12/2003 | Eversull | |
| 2004/0059277 A1 | 3/2004 | Maguire | |
| 2004/0064147 A1 | 4/2004 | Struble | |
| 2004/0106852 A1 | 6/2004 | Windheuser | |
| 2004/0249367 A1 * | 12/2004 | Saadat | A61B 1/018 606/1 |
| 2005/0059890 A1 | 3/2005 | Deal | |
| 2005/0085841 A1 | 4/2005 | Eversull | |
| 2005/0107738 A1 | 5/2005 | Slater | |
| 2005/0124918 A1 | 6/2005 | Griffin | |
| 2005/0131279 A1 | 6/2005 | Boulais | |
| 2005/0149097 A1 | 7/2005 | Regnell | |
| 2005/0154262 A1 | 7/2005 | Banik | |
| 2005/0182387 A1 | 8/2005 | Webler | |
| 2005/0222558 A1 | 10/2005 | Baxter | |
| 2005/0256508 A1 | 11/2005 | Hall | |
| 2005/0261554 A1 | 11/2005 | Scholly | |
| 2005/0261674 A1 | 11/2005 | Nobis | |
| 2006/0030753 A1 | 2/2006 | Boutillette | |
| 2006/0030864 A1 | 2/2006 | Kennedy | |
| 2006/0149127 A1 | 7/2006 | Seddiqui | |
| 2006/0262415 A1 * | 11/2006 | Forkey | G02B 23/2476 359/642 |
| 2007/0043324 A1 | 2/2007 | Shibata | |
| 2007/0043338 A1 | 2/2007 | Moll | |
| 2007/0215268 A1 | 9/2007 | Pingleton | |
| 2007/0225559 A1 | 9/2007 | Clerc | |
| 2007/0249907 A1 | 10/2007 | Boulais | |
| 2007/0293726 A1 | 12/2007 | Goldfarb | |
| 2008/0015625 A1 | 1/2008 | Ventura | |
| 2008/0045787 A1 | 2/2008 | Snay | |
| 2008/0132762 A1 | 6/2008 | Melville | |
| 2008/0154207 A1 | 6/2008 | Hardin | |
| 2008/0183035 A1 | 7/2008 | Vakharia | |
| 2008/0208133 A1 | 8/2008 | Lieberman | |
| 2008/0245371 A1 | 10/2008 | Gruber | |
| 2008/0262300 A1 | 10/2008 | Ewers | |
| 2008/0319418 A1 | 12/2008 | Chong | |
| 2009/0049698 A1 | 2/2009 | Drake | |
| 2009/0171161 A1 | 7/2009 | Ewers | |
| 2009/0281376 A1 | 11/2009 | Acosta | |
| 2010/0032470 A1 | 2/2010 | Hess et al. | |
| 2010/0121269 A1 | 5/2010 | Goldenberg | |
| 2010/0130850 A1 | 5/2010 | Pakter | |
| 2010/0145331 A1 | 6/2010 | Chrisitian | |
| 2010/0268123 A1 | 10/2010 | Callahan | |
| 2011/0245765 A1 | 10/2011 | Jacobsen | |
| 2012/0018082 A1 | 1/2012 | Kuboi | |
| 2012/0029421 A1 | 2/2012 | Drake | |
| 2012/0172663 A1 | 7/2012 | Perretta | |
| 2012/0184954 A1 | 7/2012 | Onishi | |
| 2012/0215071 A1 | 8/2012 | Mahlin | |
| 2012/0296167 A1 | 11/2012 | Chen et al. | |
| 2013/0028554 A1 | 1/2013 | Wong | |
| 2013/0046144 A1 | 2/2013 | Iede | |
| 2013/0102846 A1 * | 4/2013 | Sjostrom | A61B 1/07 600/110 |
| 2013/0109919 A1 | 5/2013 | Sugiyama et al. | |
| 2013/0172673 A1 * | 7/2013 | Kennedy, II | A61B 1/0125 600/109 |
| 2013/0253481 A1 | 9/2013 | Dewaele | |
| 2013/0289352 A1 | 10/2013 | Boulais | |
| 2014/0024951 A1 | 1/2014 | Herzlinger | |

(56) References Cited

U.S. PATENT DOCUMENTS

| | | |
|---|---|---|
| 2014/0066706 A1 | 3/2014 | McWeeney |
| 2014/0073854 A1 | 3/2014 | Vincent |
| 2014/0135576 A1 | 5/2014 | Hebert |
| 2014/0148759 A1 | 5/2014 | Mcnamara |
| 2014/0243592 A1 | 8/2014 | Kato et al. |
| 2014/0276966 A1 | 9/2014 | Ranucci |
| 2015/0231388 A1 | 8/2015 | Barker |
| 2016/0096004 A1 | 4/2016 | Genans |
| 2016/0310701 A1 | 10/2016 | Pai |
| 2017/0224956 A1 | 8/2017 | Melsheimer |
| 2017/0340193 A1 | 11/2017 | Gambhir et al. |
| 2018/0344987 A1 | 12/2018 | Lancette |
| 2019/0082940 A1 | 3/2019 | Igov |
| 2019/0117937 A1 | 4/2019 | Humphrey |
| 2019/0224458 A1 | 7/2019 | Morera |
| 2019/0224459 A1 | 7/2019 | Pedroni |

FOREIGN PATENT DOCUMENTS

| | | |
|---|---|---|
| CN | 103654694 A | 3/2014 |
| CN | 107529958 A | 10/2014 |
| CN | 104219987 A | 12/2014 |
| JP | 2013-106713 A | 6/2013 |
| WO | 02/053221 | 7/2002 |
| WO | 2004/086957 | 10/2004 |
| WO | 2012/088167 | 6/2012 |
| WO | 2016/064449 | 4/2016 |
| WO | 2016/064763 | 4/2016 |
| WO | 2016/171780 | 10/2016 |

OTHER PUBLICATIONS

U.S. Appl. No. 15/751,153, Sekowski, filed Feb. 7, 2018.
Office action from Chinese Patent Application No. 201580068469.1 dated Sep. 29, 2018 with search report and its English translation.
Office action from Chinese Patent Application No. 201580068469.1 dated Jul. 29, 2019 and its English translation.
Office action from Chinese Patent Application No. 201580068469.1 dated Apr. 14, 2020.
Office action from Chinese Patent Application No. 201580068398.5 dated Sep. 29, 2018 and its English translation.
Office action from Chinese Patent Application No. 201580068398.5 dated Aug. 2, 2019 with search report and its English translation.
Office action from Chinese Patent Application No. 201580068398.5 dated Apr. 27, 2020.
Office action from Chinese Patent Application No. 201680028488.6 dated Mar. 21, 2019 and its English translation.
Office action from Chinese Patent Application No. 201680028488.6 dated Oct. 9, 2019 and its English translation.
Office action from Chinese Patent Application No. 201680028488.6 dated May 29, 2020.
EPO extended search report from European Patent Application No. 15852255.7 dated Dec. 19, 2018.
EPO extended Search Report from European Patent Application No. 15852048.6 dated Jun. 8, 2018.
EPO partial supplementary search report from European Patent Application No. 15852048.6 dated Mar. 7, 2018.
EPO extended search report from European Patent Application No. 16783528.9 dated Jan. 7, 2019.
EPO extended search report from European Patent Application No. 20020249.7 dated Oct. 9, 2020.
PCT International Search Report from PCT/US2015/056279 dated Jan. 13, 2016.
PCT International Written Opinion from PCT/US2015/056279 dated Jan. 13, 2016.
PCT International Preliminary Report on Patentability (Chapter I) with Written Opinion from PCT/US2015/056279 dated Apr. 25, 2017.
PCT International Search Report from PCT/US2015/027170 dated Jul. 27, 2015.
PCT International Written Opinion from PCT/US2015/027170 dated Jul. 27, 2015.
PCT International Preliminary Report on Patentability (Chapter I) with Written Opinion from PCT/US2015/027170 dated Apr. 25, 2017.
From U.S. Appl. No. 15/751,153, Office Action dated Apr. 13, 2020.
From U.S. Appl. No. 15/751,150, Office Action dated Apr. 13, 2020.
From U.S. Appl. No. 15/751,150, Office Action dated Oct. 2, 2020.
International Search Report for PCT/US2016/017033 dated May 10.
Written Opinion of the International Searching Authority for PCT/US2016/017033 dated May 10, 2016.
International Preliminary Report on Patentability Chapter I for PCT/US2016/017033 dated Oct. 24, 2017.
Office action from Chinese Patent Application No. 201580068398.5 dated Aug. 4, 2021, and its machine English translation.
Office action from Chinese Patent Application No. 201580068398.5 dated Feb. 1, 2021, and its machine English translation.
Office action from Chinese Patent Application No. 201580068469.1 dated Jan. 6, 2021, and its English translation.
From U.S. Appl. No. 15/751,150, Office Action dated Jan. 24, 2022.
From U.S. Appl. No. 15/751,150, Office Action dated Jul. 19, 2021.
From U.S. Appl. No. 15/751,153, Office Action dated Dec. 21, 2020.

\* cited by examiner

| passing the proximal ends of a plurality of optic fibers through a space comprised between the walls of the imaging sensor and the inner walls of said flexible tubular jacket, then through the longitudinal lumen of the ring and the elongated member        216 |

↓

| arranging distal ends of said plurality of optic fibers extending longitudinally along the imaging sensor in said space        218 |

↓

| attaching permanently the distal ends of said plurality of optic fibers in said space        220 |

↓

| polishing said distal ends of a plurality of optic fibers attached to the imaging sensor, together with a distal end optical window of the imaging sensor |

```
┌─────────────────────────────────────────────────────────────┐
│ providing an imaging sensor having a rectangular cross       │
│ section, a proximal end of the imaging sensor being          │
│ connected to an imaging cable                    224         │
└─────────────────────────────────────────────────────────────┘
                              ↓
┌─────────────────────────────────────────────────────────────┐
│ providing a tubular shell having an inner diameter equal to  │
│ a diagonal of said rectangular cross section; a proximal end │
│ of the tubular shell being attached to a distal end of a     │
│ tensioning ring, the tensioning ring having an outer         │
│ diameter smaller than an outer diameter of the tubular shell │
│ and having a central longitudinal lumen capable of receiving │
│ said imaging cable                               226         │
└─────────────────────────────────────────────────────────────┘
                              ↓
┌─────────────────────────────────────────────────────────────┐
│ providing a flexible elongated member having an outer        │
│ diameter equal to the outer diameter of the tensioning ring, │
│ the flexible elongated member having at least a central      │
│ longitudinal lumen capable of receiving said imaging cable   │
│ and at least one lateral longitudinal tensioning lumen       │
│ capable of receiving a tensioning wire           228         │
└─────────────────────────────────────────────────────────────┘
                              ↓
┌─────────────────────────────────────────────────────────────┐
│ attaching a distal end of a tensioning wire to said          │
│ tensioning ring                                        230   │
└─────────────────────────────────────────────────────────────┘
                              ↓
┌─────────────────────────────────────────────────────────────┐
│ passing said tensioning wire through said at least one       │
│ tensioning lumen                                       232   │
└─────────────────────────────────────────────────────────────┘
                              ↓
┌─────────────────────────────────────────────────────────────┐
│ introducing said ring and said elongated member in an axial  │
│ lumen of a flexible tubular jacket, wherein the inner        │
│ diameter of the jacket is equal to or slightly larger than   │
│ the outer diameter of the ring and elongated member          │
│                                                        234   │
└─────────────────────────────────────────────────────────────┘
                              ↓
┌─────────────────────────────────────────────────────────────┐
│ passing said imaging cable through the longitudinal lumen of │
│ the tensioning ring and of the flexible elongated member 236 │
└─────────────────────────────────────────────────────────────┘
                              ↓
┌─────────────────────────────────────────────────────────────┐
│ introducing said imaging sensor in the tubular shell         │
│                                                        238   │
└─────────────────────────────────────────────────────────────┘
```

FIG. 20 passing the proximal ends of a plurality of optic fibers through a space comprised between the walls of the imaging sensor and the inner walls of the tubular shell, then through the longitudinal lumen of the ring and the elongated member
— 240 arranging the distal ends of said plurality of optic fibers longitudinally along the imaging sensor in said space
— 242 attaching permanently said distal ends of a plurality of optic fibers in said space
— 244 polishing said distal ends of a plurality of optic fibers attached to the imaging sensor, together with a distal end optical window of the imaging sensor
— 246

FIG. 21

STEERABLE MICRO-ENDOSCOPE

CROSS REFERENCE TO RELATED APPLICATIONS

This presentation application is the U.S. national phase application of a PCT Application No. PCT/US2016/017033 filed on Feb. 8, 2016, which claims priority of PCT application No. PCT/US2015/027170, filed on Apr. 22, 2015, and entitled "STEERABLE MICRO-ENDOSCOPE", which is hereby incorporated by reference and which claims priority to U.S. Ser. No. 62/066,340, filed Oct. 20, 2014 which is hereby incorporated by reference.

This presentation claims priority of PCT application No. PCT/US2015/056279, filed on Oct. 19, 2015 and entitled "STEERABLE MICRO-ENDOSCOPE", which is hereby incorporated by reference.

FIELD OF THE DISCLOSURE

This presentation relates to steerable micro devices such as endoscopes of reduced size, for example for medical use, and methods of making thereof.

BACKGROUND

Various commercially available endoscopes exist for introducing into the body vessels and cavities a variety of surgical tools, fluids such as radiographic contrast materials, angioplasty balloons, fiberoptic scopes, laser lights, and cutting instruments. Also, various techniques and systems have been developed for guiding or steering the catheters in the body vessels and cavities for use of these tools, fluids, and other materials.

Examples of such guiding or steering techniques and systems for catheters or endoscopes may be seen in: U.S. Pat. No. 5,342,299 to Snoke entitled "steerable catheter"; in WO2004086957 to Banik, entitled "Single use endoscopic imaging system"; in US20140135576 to Hebert, entitled "Coaxial micro-endoscope"; in U.S. Pat. No. 8,517,921 to Tremaglio, entitled "Endoscopic instrument having reduced diameter flexible shaft"; in U.S. Pat. No. 8,262,563 to Bakos, entitled "Endoscopic translumenal articulatable steerable overtube"; in U.S. Pat. No. 8,320,650 to Demos, entitled "In vivo spectral micro-imaging of tissue"; in US 2008/0319418 to Chong, entitled "Catheter Steering Device"; in WO 02/053221 to Gaber, entitled "Deflectable Guiding Apparatus"; in U.S. Pat. No. 4,580,551 to Siegmund, entitled "Flexible Plastic Tube for Endoscope and the Like"; in U.S. Pat. No. 5,325,845 to Adair, entitled "Steerable Sheath for Use with Selected Removable Optical Catheter"; in U.S. Pat. No. 4,798,193 to Giesy, entitled "Protective Sheath Instrument Carrier"; in U.S. Pat. No. 4,788,967 to Leda; entitled "Endoscope"; in U.S. Pat. No. 7,033,317 to Pruitt, entitled "disposable endoscope and method of making a disposable endoscope; in U.S. Pat. No. 5,197,457 to Adair, entitled "deformable and removable sheath for optical catheter".

However, there exists a need for a steerable micro-device, such as a micro-endoscope with a steerable distal end, which would be particularly simple and economical to manufacture.

SUMMARY OF THE DISCLOSURE

An object of this presentation relates to a steerable micro-endoscope, preferably comprising optical fibers for conducting light to its distal end and comprising a camera or imaging sensor at its distal end. Preferably, the camera or imaging sensor has a rectangular or square cross section and comprises a rectangular or square CMOS or CCD sensor.

An object of this presentation relates to a micro-device that is steerable in that it has an elongated member with a distal portion that bends in a remotely controlled way. The elongated member can also be provided to rotate axially in a controllable way.

An object of this presentation relates to a micro-endoscope that has an elongated member with a diameter of 2 millimeter or less; preferably of 15 millimeter or less.

These and other objects, features, and advantages are provided in an endoscope comprising: a tubular elongated member having a longitudinal axis, a proximal end and a distal end; at least one tensioning wire arranged in a tensioning lumen along one side of the elongated member, between the proximal end and the distal end of the elongated member; a head arranged at the distal end of the elongated member, the head comprising: a tubular tensioning ring attached to the distal end of the tensioning wire, the tensioning ring having a same external diameter as the elongated member; an imaging sensor having a rectangular cross section, arranged at a distal end of the head; and a tubular distal shell arranged longitudinally around the imaging sensor, the distal shell having an inner diameter identical to or slightly larger than a diagonal of the rectangular cross section of the imaging sensor; wherein a tubular jacket sheathes the elongated member and the tensioning ring of the head. According to an embodiment of this presentation, "slightly larger than" can mean larger by up to 10 microns. According to an embodiment of this presentation, "slightly larger than" can mean larger by up to 5 microns. According to an embodiment of this presentation, "slightly larger than" can mean larger by up to 2.5 microns.

According to an embodiment of this presentation, the distal shell of the head has an outer diameter identical to the outer diameter of the tubular jacket.

According to an embodiment of this presentation, a distal end of a plurality of optical fibers is arranged between the inner diameter of the distal shell and lateral walls of the imaging sensor; the optical fibers passing through a lumen in the tensioning ring and a lumen in the elongated member.

According to an embodiment of this presentation, the distal shell has a proximal end that is attached to a distal end of the tensioning ring; the proximal end of the tensioning ring being abutted to the distal end of the elongated member.

According to an embodiment of this presentation, the tensioning ring comprises a longitudinal cut extending from a proximal end of the tensioning ring; the distal end of the tensioning wire extending along and being welded into the longitudinal cut such that the tensioning wire does not extend radially beyond the external diameter of the tensioning ring.

According to an embodiment of this presentation, the tensioning lumen of the elongated member is a longitudinal groove cut in the outer surface of the elongated member; the tensioning wire being retained in the groove by the tubular sheath.

According to an embodiment of this presentation, the elongated member comprises a central lumen; the central lumen having a narrower cross section opposite the longitudinal groove in the outer surface of the elongated member.

According to an embodiment of this presentation, the elongated member comprises two tensioning lumens and two tensioning wires, arranged symmetrically with respect to the longitudinal axis of the elongated member.

According to an embodiment of this presentation, the distal shell is formed by the distal end of the tubular jacket; the tubular jacket sheathing the elongated member, the tensioning ring and the imaging sensor of the head; the proximal end of the tensioning ring being abutted to the distal end of the elongated member.

According to an embodiment of this presentation, the elongated member comprises two longitudinal tensioning lumens and two tensioning wires, arranged symmetrically with respect to the longitudinal axis of the elongated member.

According to an embodiment of this presentation, the tensioning ring comprises: two longitudinal recesses cut in an inner wall of the tensioning ring, and aligned with the longitudinal tensioning lumens of the elongated member, and two radial recesses joining the longitudinal recesses to a circumferential outer trench cut in an outer wall of the tensioning ring; the distal ends of the two tensioning wires being arranged in said two longitudinal recesses and said two radial recesses, and being joined in said circumferential outer trench.

According to an embodiment of this presentation, the longitudinal tensioning lumens of the tubular elongated member are formed in the thickness of the elongated member.

According to an embodiment of this presentation, the elongated member comprises a central lumen; the central lumen having a narrower cross section near the longitudinal tensioning lumens.

According to an embodiment of this presentation, a distal portion of the elongated member has a first durometer; the portion of the elongated member between the distal portion and the proximal end of the elongated member having a second durometer higher than the first durometer.

According to an embodiment of this presentation, the elongated member is made of a single material; the distal portion of the elongated member comprising a series of cuts or recesses removing portions of the elongated member along the tensioning lumen along planes generally normal to the longitudinal axis of the elongated member.

An embodiment of this presentation also relates to a method of making an endoscope comprising: providing an imaging sensor having a rectangular cross section; a proximal end of the imaging sensor being connected to an imaging cable; providing a tensioning ring having an outer diameter equal to a diagonal of said rectangular cross section, the ring having a central longitudinal lumen capable of receiving said imaging cable; providing a flexible elongated member having an outer diameter equal to said diagonal of said rectangular cross section, the flexible elongated member having at least a central longitudinal lumen capable of receiving said imaging cable and at least one lateral longitudinal tensioning lumen capable of receiving a tensioning wire; attaching a distal end of a tensioning wire to said tensioning ring; passing said tensioning wire through said at least one tensioning lumen until the tensioning ring is arranged at a distal end of the flexible elongated member; introducing said ring and said elongated member in an axial lumen of a flexible tubular jacket, wherein the inner diameter of the jacket is equal to or slightly larger than said diagonal of said rectangular cross section, such that said ring lies inside the flexible tubular jacket beyond a distal end of the flexible tubular jacket; passing said imaging cable through the longitudinal lumen of the ring and through the longitudinal lumen of the flexible elongated member from the distal end of said flexible tubular jacket; introducing said imaging sensor in the axial lumen of the distal end of said flexible tubular jacket.

According to an embodiment of this presentation, the method further comprises: passing the proximal ends of a plurality of optic fibers through a space comprised between the walls of the imaging sensor and the inner walls of said flexible tubular jacket, then through the longitudinal lumen of the ring and the elongated member; arranging distal ends of said plurality of optic fibers extending longitudinally along the imaging sensor in said space; and attaching permanently the distal ends of said plurality of optic fibers in said space.

According to an embodiment of this presentation, the method further comprises: polishing said distal ends of a plurality of optic fibers attached to the imaging sensor, together with a distal end optical window of the imaging sensor.

An embodiment of this presentation also relates to a method of making an endoscope comprising: providing an imaging sensor having a rectangular cross section, a proximal end of the imaging sensor being connected to an imaging cable; providing a tubular shell having an inner diameter equal to or slightly larger than a diagonal of said rectangular cross section; a proximal end of the tubular shell being attached to a distal end of a tensioning ring, the tensioning ring having an outer diameter smaller than an outer diameter of the tubular shell and having a central longitudinal lumen capable of receiving said imaging cable; providing a flexible elongated member having an outer diameter equal to the outer diameter of the tensioning ring, the flexible elongated member having at least a central longitudinal lumen capable of receiving said imaging cable and at least one lateral longitudinal tensioning lumen capable of receiving a tensioning wire; attaching a distal end of a tensioning wire to said tensioning ring; passing said tensioning wire through said at least one tensioning lumen; introducing said ring and said elongated member in an axial lumen of a flexible tubular jacket, wherein the inner diameter of the jacket is equal to or slightly larger than the outer diameter of the ring and elongated member; passing said imaging cable through the longitudinal lumen of the tensioning ring and of the flexible elongated member; and introducing said imaging sensor in the tubular shell.

According to an embodiment of this presentation, the outer diameter of the jacket is equal to the outer diameter of the tubular shell.

According to an embodiment of this presentation, the method further comprises: passing the proximal ends of a plurality of optic fibers through a space comprised between the walls of the imaging sensor and the inner walls of the tubular shell, then through the longitudinal lumen of the ring and the elongated member; arranging the distal ends of said plurality of optic fibers longitudinally along the imaging sensor in said space; and attaching permanently said distal ends of a plurality of optic fibers in said space.

According to an embodiment of this presentation, the method further comprises polishing said distal ends of a plurality of optic fibers attached to the imaging sensor, together with a distal end optical window of the imaging sensor.

An embodiment of this presentation also relates to an endoscope comprising a cylindrical elongated member having a distal end and a proximal end, the elongated member comprising at least a first lumen and a second lumen, a first tensioning wire running in the first lumen and a second tensioning wire running in the second lumen, the distal ends of the tensioning wires being attached at the distal end of the elongated member and the proximal ends of the tensioning wires exiting the lumens at the proximal end of the elongated member; the elongated member and the first and second lumens being arranged such that the distal portion of the elongated member bends in a first direction when the proximal end of the first tensioning wire is pulled and in a second direction when the proximal end of the second tensioning wire is pulled; wherein the proximal end of the elongated member is coupled to a handle, the handle and the elongated member forming a T-shaped arrangement wherein the leg of the T is the elongated member and the head of the T is the handle; the handle comprising a lever arranged such that: compressing a first portion of the handle, located on one side of the proximal end of the elongated member, pulls the first tensioning wire; and compressing a second portion of the handle, located on the other side of the proximal end of the elongated member, pulls the second tensioning wire.

According to an embodiment of this presentation, the handle is shaped such that: the handle can be held in a hand of a user, with the elongated member passing between two fingers of said hand of a user; wherein tightening the grip on the handle with the side of the hand closer to the index compresses the first portion of the handle; and tightening the grip on the handle with the side of the hand closer to the auricular compresses the second portion of the handle.

BRIEF DESCRIPTION OF THE DRAWINGS

FIG. 19 is an organigram describing possible further steps of the method illustrated in FIG. 18.

FIG. 20 is an organigram describing a method of making an endoscope such as illustrated in FIG. 5.

FIG. 21 is an organigram describing possible further steps of the method illustrated in FIG. 20.

DETAILED DESCRIPTION

In the following description, numerous specific details are set forth to clearly describe various specific embodiments disclosed herein. One skilled in the art, however, will understand that the presently claimed invention may be practiced without all of the specific details discussed below. In other instances, well known features have not been described so as not to obscure the invention. The same references designate the same elements in the figures.

Figure 1:
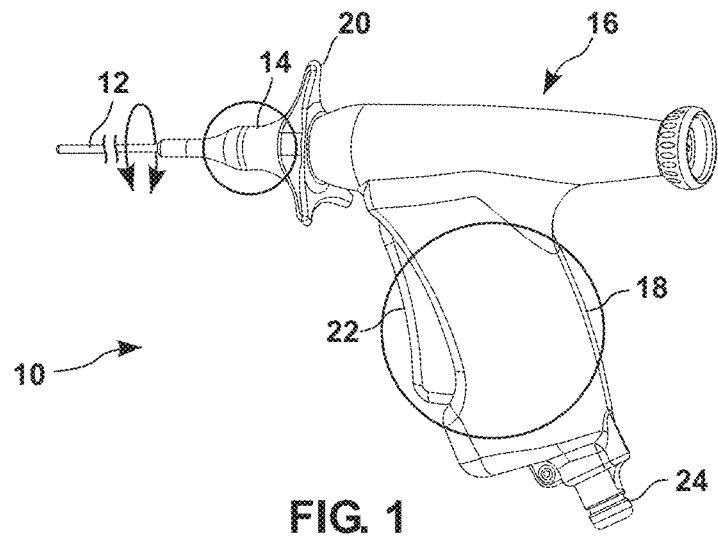
FIG. 1 is an elevation view of an endoscope according to an embodiment of this presentation.

FIG. 1 is an elevation view of a steerable micro-device or endoscope 10 according to an embodiment of this presentation, comprising a sheathed elongated member 12 having a distal end and a proximal end; the proximal end of the sheathed elongated member 12 being attached to a base 14. According to an embodiment of this presentation, base 14 is rotatable around a longitudinal axis of the sheathed elongated member with respect to a proximal housing 16 which can comprise a handle 18. According to an embodiment of this presentation, base 14 is coupled to a knob 20 allowing to controllably rotate the base 14, and handle 18 comprises a trigger 22 allowing to controllably pull one or more tensioning wires (detailed hereafter) in the sheathed elongated member 12, to controllably bend a distal portion of the sheathed elongated member 12. In an embodiment, trigger 22 is provided for pivoting in two directions, where pivoting the trigger in each of the two directions pulls each of two tensioning wires in the sheathed elongated member 12. Trigger 22 can comprise a lock for locking the tensioning wire(s) pulled along a desired length. Knob 20 can comprise a lock for controllably locking base 14 rotated along a desired angle.

According to an embodiment of this presentation, housing 16 is provided for receiving a cable 24 for providing light and/or power to the endoscope and for receiving visualization data from an imaging sensor arranged at the distal end of the sheathed elongated member, as will be detailed hereafter.

Details of implementation of the housing, tensioning wire actuation structures and rotational structures of endoscope 10, as well as of the sheathed elongated member 12, can for example be found in PCT application No. PCT/US2015/027170, filed on Apr. 22, 2015 and entitled "STEERABLE MICRO-ENDOSCOPE", and are hereby incorporated by reference.

Generally, when a tensioning wire is pulled on the proximal end, a distal section of the sheathed elongated member, provided for being easily compressed at least in an plane including the longitudinal axis of the elongated member and comprising the tensioning wire, compresses first before a less compressible, proximal, section and because the pull wire is not in the center of the elongated member, but instead in a tensioning lumen on the side of the elongated member, it results in the more compressible section to compress around the tensioning wire and bend. The amount of the bend is directly proportional to the force applied to the wire, the ratio of hardness between compressible and less compressible sections of the elongated member and the distance of the pull wire from the center of the extrusion/elongated member. Combined with a rotation of the elongated member, such embodiment allows a 360° navigation of the distal end of the elongated member. A torque braid jacket sheathing the elongated member helps providing a rotational response of the sheathed elongated member to torque forces without compromising flexibility of the sheathed elongated member. A micro-endoscope according to embodiments of this presentation can be used for diagnosis in micro invasive procedures in many cases eliminating a need for costly MRI's. The same micro-endoscopes can be equipped with a tool to perform biopsies in micro-invasive procedures in doctor's office requiring only local anesthetic in contrast to surgery done in the hospital under general anesthesia. The elongated member can be made more or less compressible by using materials having a different durometer or by using a single material where recesses are cut or dug to render the material more compressible.

Figure 2:
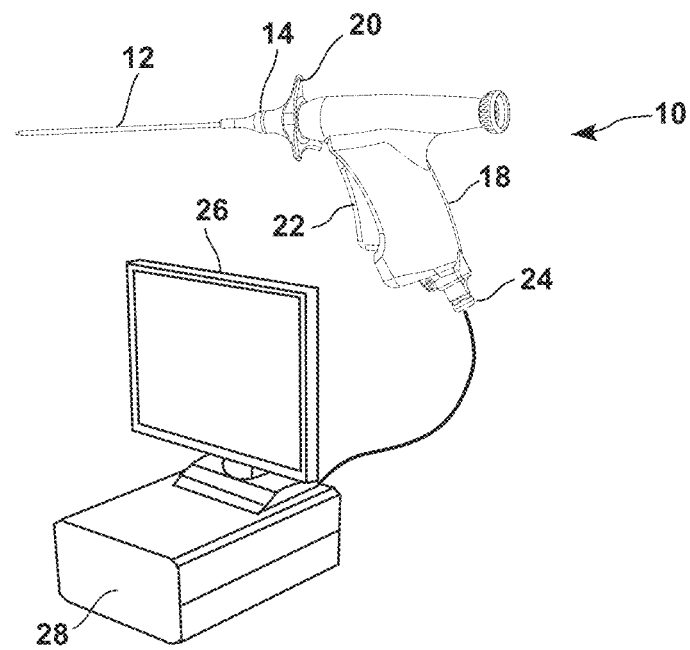
FIG. 2 is an elevation view of an endoscope according to an embodiment of this presentation, connected to an imaging device and a source of power.

FIG. 2 is an elevation view showing endoscope 10 connected to an imaging device 26 for displaying imaging data acquired at the distal end of the sheathed elongated member 12, and connected to a source of power and/or light 28 for providing light and/or power to the endoscope.

Figure 3:
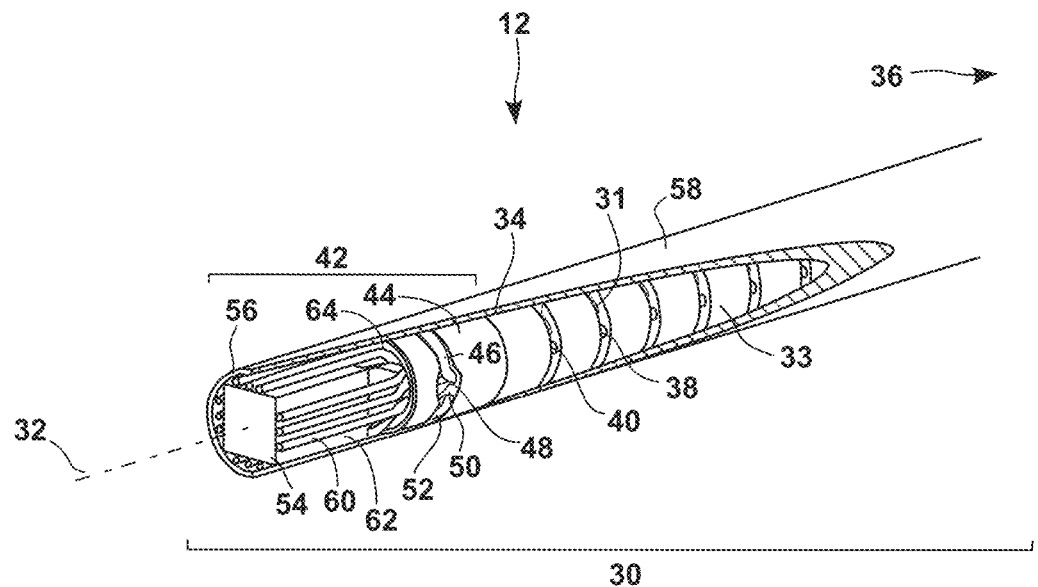
FIG. 3 is a partly cut away elevation view of the distal portion of the sheathed elongated member of an endoscope according to an embodiment of this presentation.

FIG. 3 is a partly cut away elevation view of a distal portion 30 of the sheathed elongated member 12 of an endoscope 10 (not shown) according to an embodiment of this presentation. According to an embodiment of this presentation, the sheathed elongated member 12 has a longitudinal axis 32 and comprises a tubular (i.e. having a longitudinal lumen 31) elongated member 33 having a distal end 34 and a proximal end 36.

According to an embodiment of this presentation, at least one tensioning wire 38 is arranged in a tensioning lumen 40 along one side of the elongated member 33, between the proximal end 34 and the distal end 36 of the elongated member 33.

According to an embodiment of this presentation, elongated member 33 comprises two longitudinal tensioning lumens 40 and two tensioning wires 38, arranged symmetrically with respect to longitudinal axis 32. According to an embodiment of this presentation, elongated member 33 can also comprise more than two longitudinal tensioning lumens and a corresponding number of tensioning wires.

According to an embodiment of this presentation, the distal portion 30 of the sheathed elongated member 12 comprises a head 42 arranged at the distal end 34 of the elongated member 33, the head comprising: a tubular tensioning ring 44 attached to a distal end 46 of the tensioning wires 38, the tensioning ring 44 having a same external diameter as the elongated member 33.

According to an embodiment of this presentation, the tensioning ring 44 comprises two longitudinal recesses 48 cut in an inner wall of the tensioning ring 44 and aligned with the longitudinal tensioning lumens 40 of the elongated member 33, and two axial recesses 50 joining the longitudinal recesses 48 to a circumferential outer trench 52 cut in an outer wall of the tensioning ring 44. According to an embodiment of this presentation, the distal ends 46 of the two tensioning wires 38 are arranged in the two longitudinal recesses 48 and the two axial recesses 50, and are joined in said circumferential outer trench 52.

According to an embodiment of this presentation, the longitudinal tensioning lumens 40 of the tubular elongated member 33 are formed in the thickness of the elongated member 33. As outlined previously, according to an embodiment of this presentation the elongated member 33 comprises a central lumen 31. According to an embodiment of this presentation, the central lumen 31 has a narrower cross section near the longitudinal tensioning lumens 40.

According to an embodiment of this presentation, head 42 further comprises an imaging sensor 54 having a rectangular cross section, arranged at a distal end of the head 42; and a tubular distal shell 56 arranged longitudinally around the imaging sensor 54. According to an embodiment of this presentation, the distal shell 56 has an inner diameter identical to or slightly larger than a diagonal of the rectangular cross section of the imaging sensor 54. According to an embodiment of this presentation, a tubular jacket 58 sheathes the elongated member 33 and the tensioning ring of the head. According to an embodiment of this presentation, the tubular jacket 58 has an inner diameter equal to, or slightly larger than, the outer diameter of the elongated member 33 and the tensioning ring of the head. According to an embodiment of this presentation, the distal shell 56 of the head has an outer diameter identical to the outer diameter of the tubular jacket 58. According to an embodiment of this presentation as illustrated in FIG. 3, the distal shell 56 of the head is formed by the distal end of the tubular jacket 58. It follows that in the embodiment of this presentation as illustrated in FIG. 3, the total diameter of the sheathed elongated member 12 is equal to the diagonal of the imaging sensor 54 plus two times the thickness of the wall of jacket 58. The jacket 82 can include a torque mesh. Glue can be used to maintain the imaging sensor at in the jacket 82 if necessary.

According to an embodiment of this presentation, a distal end of a plurality of optical fibers 60 extending longitudinally along the imaging sensor 54 is arranged between the inner diameter of the distal shell 56 and the lateral walls 62 of the imaging sensor 54; the optical fibers 60 passing through a lumen 64 in the tensioning ring 44 and the lumen 31 in the elongated member 33. For clarity, three optical fibers 60 are shown on each side 62 of the imaging sensor 54 in FIG. 3, but according to an embodiment of this presentation, up to several hundreds of optical fibers can be arranged on the sides 62 of imaging sensor 54.

According to an embodiment of this presentation, the distal ends of the optical fibers 60 can be attached to the sides 62 of imaging sensor 54 by:

arranging said distal ends of the optic fibers 60 in a space comprised between the walls 62 of the imaging sensor 54 and the inner walls of a mounting tube having an inner diameter equal to said diagonal of said rectangular cross section; attaching permanently said distal ends of the optic fibers 60 to the imaging sensor 54, for example by introducing a glue or resin in the spaces remaining between the fibers; and removing said mounting tube when the glue or resin has set.

According to an embodiment of this presentation, the distal ends of the optic fibers 60 can be polished, together with a distal end (for example comprising an optical window) of the imaging sensor 54 after they are attached to the imaging sensor 54.

Figure 4:
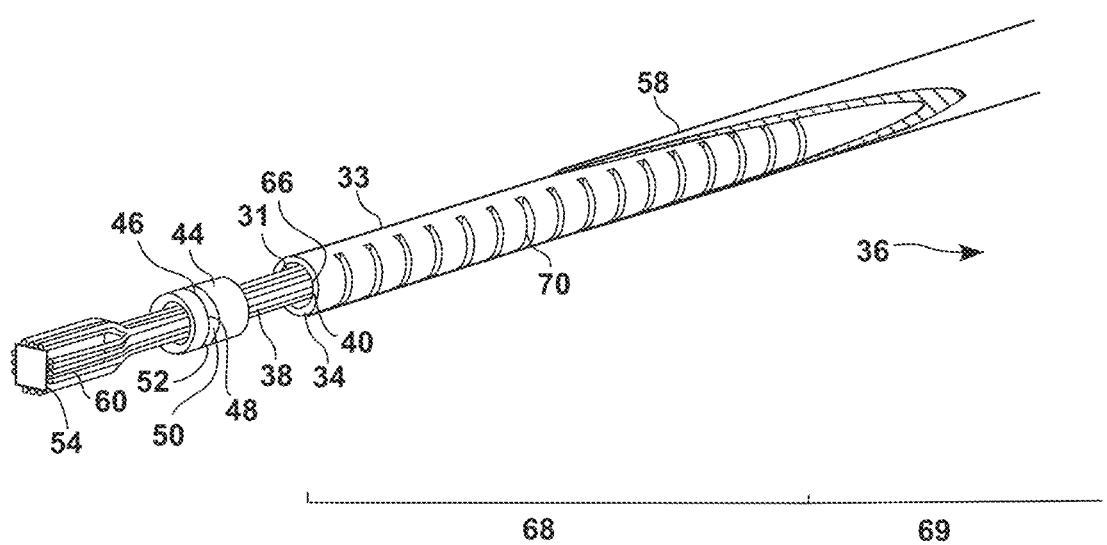
FIG. 4 is a partly cut away elevation view of the distal portion of the sheathed elongated member shown in FIG. 3.

FIG. 4 is a partly cut away elevation view of the distal portion 30 of the sheathed elongated member 12 shown in FIG. 3, where some elements are shown distanced from each other for clarity.

Hence, FIG. 4 shows more clearly the tubular elongated member 33, having a longitudinal lumen 31, a distal end 34 and a proximal end 36.

FIG. 4 also shows more clearly a tensioning wire 38 arranged in a tensioning lumen 40 along a side of the elongated member 33, between the proximal end 34 and the distal end 36 of the elongated member 33.

FIG. 4 also shows more clearly tubular tensioning ring 44 attached to a distal end 46 of the tensioning wire 38, having two longitudinal recesses 48 (one shown) cut in an inner wall of the tensioning ring 44 and aligned with the longitudinal tensioning lumens 40 (one shown) of the elongated member 33, and two axial recesses 50 (one shown) joining the longitudinal recesses 48 to a circumferential outer trench 52 cut in an outer wall of the tensioning ring 44.

FIG. 4 also shows more clearly that an imaging cable 49, attached to the proximal end of imaging sensor 54, passes through the longitudinal lumen 64 of the ring 44 and the longitudinal lumen 31 of the elongated member 33 toward the proximal end of the elongated member 33. According to an embodiment of this presentation, imaging cable 49 can be arranged in the middle of the optical fibers 60, which also pass through the longitudinal lumen of the ring 44 and the longitudinal lumen 31 of the elongated member 33 toward the proximal end of the elongated member 33.

FIG. 4 also shows more clearly that the central lumen 31 of elongated member 33 has a narrower cross section in the vicinity 66 of the longitudinal tensioning lumens 40.

According to an embodiment of this presentation, the distal portion 68 of the elongated member 33 has a first durometer and the portion 69 of the elongated member 33 between the distal portion 68 and the proximal end 36 of the elongated member 33 has a second durometer higher than the first durometer. According to an embodiment of this presentation, the elongated member 33 can be made of a single material, the distal portion of the elongated member 33 comprising a series of cuts or recesses 70 removing portions of the elongated member 33 along the tensioning lumen 40 along planes generally normal to the longitudinal axis 32 of the elongated member 33.

Details regarding other embodiments of the elongated member having two durometers can be found in PCT application No. PCT/US2015/027170, filed on Apr. 22, 2015 and entitled "STEERABLE MICRO-ENDOSCOPE", and are hereby incorporated by reference.

Figure 5:
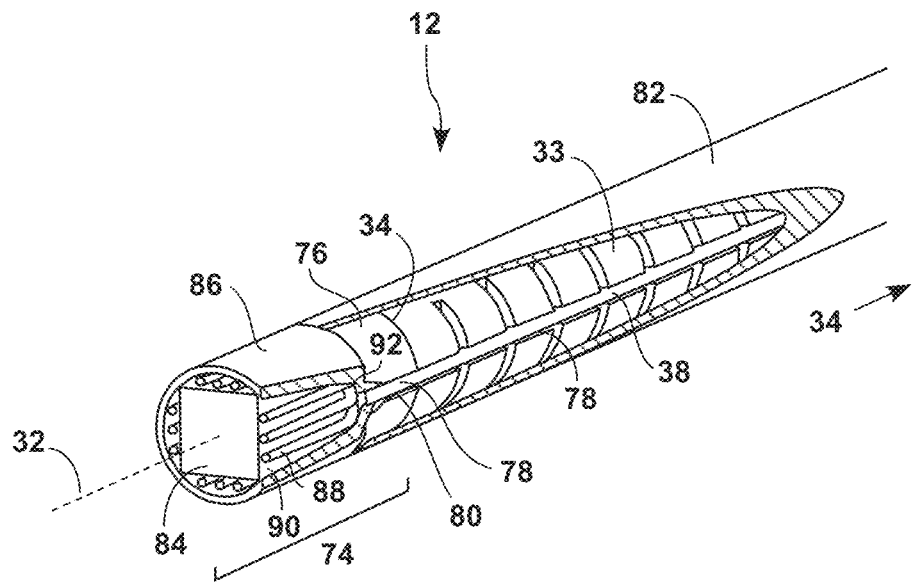
FIG. 5 is a partly cut away elevation view of the distal portion of the sheathed elongated member of an endoscope according to an embodiment of this presentation.

FIG. 5 is a partly cut away elevation view of the distal portion of the sheathed elongated member 12 of an endoscope 10 (not shown) according to another embodiment of this presentation. According to an embodiment of this presentation, the sheathed elongated member 12 has a longitudinal axis 32 and comprises a tubular (i.e. with a longitudinal lumen) elongated member 33 having a distal end 34 and a proximal end 36.

According to an embodiment of this presentation, at least one tensioning wire 38 is arranged in a tensioning lumen 72 along one side of the elongated member 33, between the proximal end 34 and the distal end 36 of the elongated member 33.

According to an embodiment of this presentation, elongated member 33 comprises two longitudinal tensioning lumens 72 (one shown) and two tensioning wires 38 (one shown), arranged symmetrically with respect to longitudinal axis 32. According to an embodiment of this presentation, elongated member 33 can also comprise more than two longitudinal tensioning lumens and a corresponding number of tensioning wires.

According to an embodiment of this presentation, the distal portion of the sheathed elongated member 12 comprises a head 74 arranged at the distal end 34 of the elongated member 33, the head 74 comprising: a tubular tensioning ring 76 attached to a distal end 78 of each tensioning wire 38, the tensioning ring 76 having a same external diameter as the elongated member 33. According to an embodiment of this presentation, the tensioning ring 76 comprises a longitudinal cut 80 for each tensioning wire, extending from a proximal end of the tensioning ring and provided for being aligned with the tensioning lumens 72. According to an embodiment of this presentation, the distal end 78 of each tensioning wire 38 extends along and is welded into the corresponding longitudinal cut 80. Preferably, the distal ends 78 of the tensioning wires are welded in the cuts 80 such that the tensioning wires do not extend radially beyond the external diameter of the tensioning ring 76.

According to an embodiment of this presentation, each tensioning lumen 72 of the elongated member 33 comprises a longitudinal groove cut in the outer surface of the elongated member 33; the tensioning wire being retained in the groove by the tubular jacket 82 that sheathes the elongated member 33.

According to an embodiment of this presentation, head 74 further comprises an imaging sensor 84 having a rectangular cross section, arranged at a distal end of the head 74; and a tubular distal shell 86 arranged longitudinally around the imaging sensor 84, the distal shell 86 having an inner diameter identical to a diagonal of the rectangular cross section of the imaging sensor 84.

According to an embodiment of this presentation, distal shell 86 has a proximal end that is attached to a distal end of the tensioning ring 76; the proximal end of the tensioning ring 76 being abutted to the distal end 34 of the elongated member 33.

According to an embodiment of this presentation, a tubular jacket 82 sheathes the elongated member 33 and the tensioning ring 76 of the head 74. According to an embodiment of this presentation, the distal shell 86 of the head 74 has an outer diameter identical to the outer diameter of the tubular jacket 82.

It follows that in the embodiment of this presentation as illustrated in FIG. 5, the total diameter of the sheathed elongated member 12 is equal to the diagonal of the imaging sensor 84 plus two times the thickness of the wall of distal shell 86. According to an embodiment of this presentation, the wall of distal shell 86 can be thinner than the wall of the jacket 82. The jacket 82 can include a torque mesh. According to an embodiment of this presentation, the inner diameter of distal shell 86 can be equal to the outer diameter of tensioning ring 76 and the distal portion of tensioning ring 76 can be introduced into the proximal portion of distal shell 86 prior to attaching permanently (e.g. by welding) the two together.

According to an embodiment of this presentation, a distal end of a plurality of optical fibers 88 extending longitudinally along the imaging sensor 84 is arranged between the inner diameter of the distal shell 86 and the lateral walls 90 of the imaging sensor 84; the optical fibers 88 passing through a lumen 92 in the tensioning ring 76 and the lumen in the elongated member 33. For clarity, three optical fibers 88 are shown on each side 90 of the imaging sensor 84 in FIG. 5, but according to an embodiment of this presentation, up to several hundreds of optical fibers can be arranged on the sides 90 of imaging sensor 84.

According to an embodiment of this presentation, the distal ends of the optical fibers 88 can be attached to the sides 90 of imaging sensor 84 by:

arranging said distal ends of the optic fibers 88 in the space comprised between the walls 90 of the imaging sensor 84 and the inner walls of the distal shell 86; and attaching permanently said distal ends of the optic fibers 88 to the imaging sensor 84, for example by introducing a glue or resin in the spaces remaining between the fibers and letting the glue or resin set.

According to an embodiment of this presentation, the distal ends of the optic fibers 88 can be polished, together with a distal end (for example comprising an optical window) of the imaging sensor 84 after they are attached to the imaging sensor 84.

Figure 6:
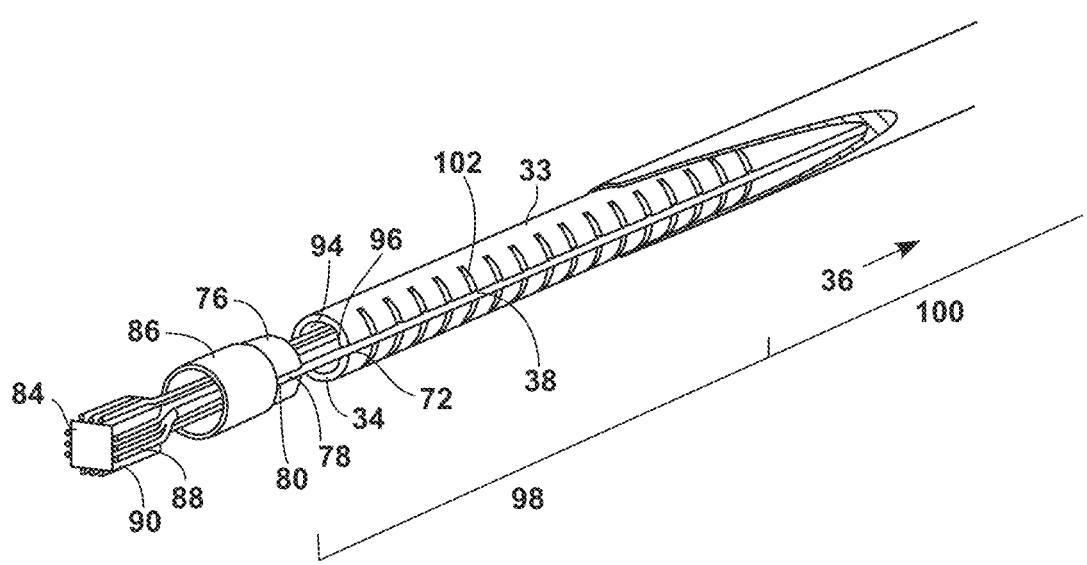
FIG. 6 is a partly cut away elevation view of the distal portion of the sheathed elongated member shown in FIG. 5.

FIG. 6 is a partly cut away elevation view of the distal portion of the sheathed elongated member 12 shown in FIG. 5, where some elements are shown distanced from each other for clarity.

Hence, FIG. 6 shows more clearly the tubular elongated member 33, having a longitudinal lumen 94, a distal end 34 and a proximal end 36.

FIG. 6 also shows more clearly a tensioning wire 38 arranged in a tensioning lumen 72 along a side of the elongated member 33, between the proximal end 34 and the distal end 36 of the elongated member 33.

FIG. 6 also shows more clearly tubular tensioning ring 76 attached to a distal end 78 of the tensioning wire 38, having two longitudinal recesses 80 (one shown) cut through the wall of the tensioning ring 76 and aligned with the longitudinal tensioning lumens 72 (one shown) of the elongated member 33.

FIG. 6 also shows more clearly that an imaging cable 95, attached to the proximal end of imaging sensor 84, passes through the longitudinal lumen of the ring 76 and the longitudinal lumen 94 of the elongated member 33 toward the proximal end of the elongated member 33. According to an embodiment of this presentation, imaging cable 95 can be arranged in the middle of the optical fibers 88, which also pass through the longitudinal lumen of the ring 76 and the longitudinal lumen 94 of the elongated member 33 toward the proximal end of the elongated member 33.

FIG. 6 also shows more clearly that the central lumen 94 of elongated member 33 has a narrower cross section in the vicinity 96 of the longitudinal tensioning lumens/grooves 72.

According to an embodiment of this presentation, the distal portion 98 of the elongated member 33 has a first durometer and the portion 100 of the elongated member 33 between the distal portion 98 and the proximal end 36 of the elongated member 33 has a second durometer higher than the first durometer. According to an embodiment of this presentation, the elongated member 33 can be made of a single material, the distal portion of the elongated member 33 comprising a series of cuts or recesses 102 removing portions of the elongated member 33 along the tensioning lumen 72 along planes generally normal to the longitudinal axis 32 of the elongated member 33.

Details regarding how to make other embodiments of an elongated member 33 having two durometers can be found in PCT application No. PCT/US2015/027170, filed on Apr. 22, 2015 and entitled "STEERABLE MICRO-ENDOSCOPE", and are hereby incorporated by reference.

Figure 7:
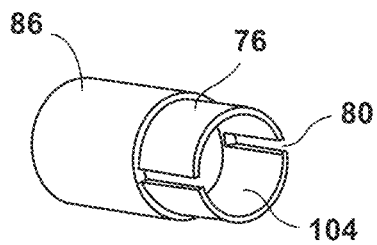
FIG. 7 is an elevation view of a distal shell attached to a tensioning ring according to an embodiment of this presentation.

FIG. 7 is an elevation view of the distal shell 86 with its proximal end attached to the distal end of the tensioning ring 76; two longitudinal recesses 80 being cut in the wall of the tensioning ring 76 from the proximal end of tensioning ring 76. According to an embodiment of this presentation, the longitudinal recess can be as long as tensioning ring 76, or shorter. According to an embodiment of this presentation, the tensioning ring 76 comprises a lumen 104 through which the optical fibers and a cable connected to the imaging sensor are passed.

Figure 8:
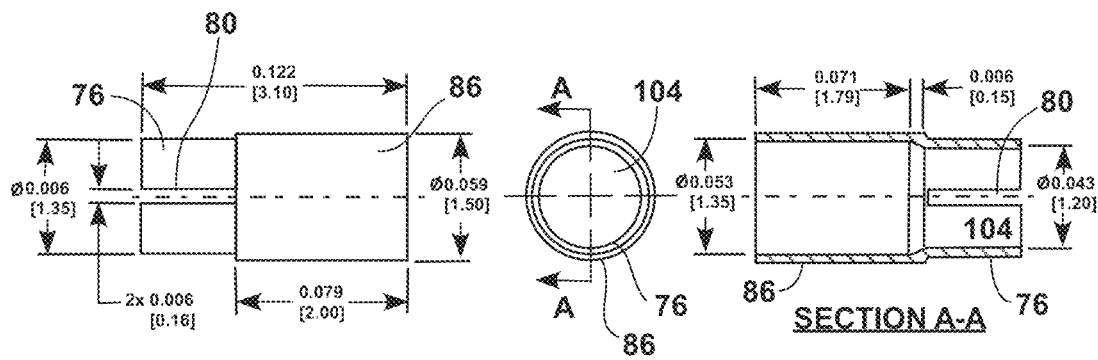
FIG. 8 comprises side, front and cross-section views of a distal shell attached to a tensioning ring according to an embodiment of this presentation.

FIG. 8 comprises, from left to right, a side view, a front view and a longitudinal cross-section of distal shell 86 attached to a tensioning ring 76 according to an embodiment of this presentation, showing exemplary sizes according to an embodiment of this presentation where the outer diameter of distal shell 86 is of 1.5 mm; the inner diameter of the distal shell 86 is identical to the outer diameter of tensioning ring and is 1.35 mm (for a jacket having an outer diameter of 1.5 mm and a wall thickness of 0.075 mm); and the inner diameter of the tensioning ring is 1.2 mm. According to an embodiment of this presentation, distal shell 86 and tensioning ring 76 can be formed out of two sections of metal tube attached together, or they can be lathed out of a single metal piece together.

Figure 9:
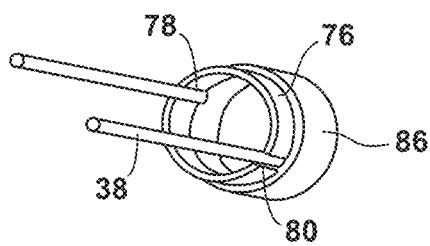
FIG. 9 is an elevation view of a distal shell attached to a tensioning ring as shown in FIG. 8 and to tensioning wires according to an embodiment of this presentation.

FIG. 9 is an elevation view of the distal shell 86 with its proximal end attached to the distal end of the tensioning ring 76 of FIG. 8; two longitudinal recesses 80 being cut in a length of the wall of the tensioning ring 76 from the proximal end of tensioning ring 76 and the distal ends 78 of the tensioning wires 38 being welded into the recesses 80.

Figure 10:
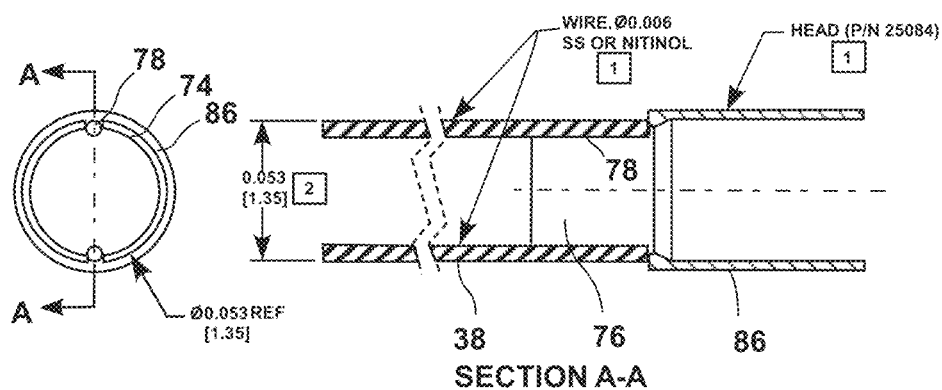
FIG. 10 comprises front and cross-section views of a distal shell attached to a tensioning ring as shown in FIG. 8 and to tensioning wires according to an embodiment of this presentation.

FIG. 10 comprises, from left to right, a front view and a longitudinal cross-section of distal shell 86 attached to a tensioning ring 76 and to the distal ends 78 of the tensioning wires 38; showing exemplary sizes according to an embodiment of this presentation where the outer diameter of tensioning ring is 1.35 mm and the diameter of the tensioning wire is 0.15 mm.

Figure 11:
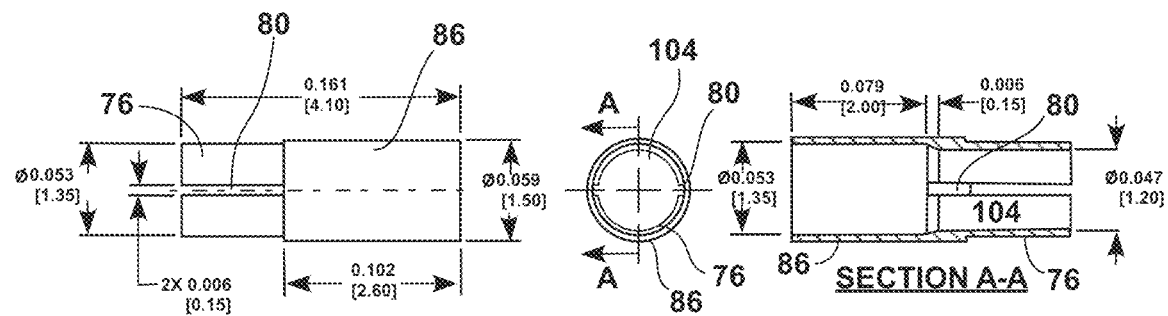
FIG. 11 comprises side, front and cross-section views of a distal shell attached to a tensioning ring according to an embodiment of this presentation.

FIG. 11 comprises, from left to right, a side view, a front view and a longitudinal cross-section of distal shell 86 attached to a tensioning ring 76 according to another embodiment of this presentation, showing exemplary sizes according to an embodiment of this presentation where the outer diameter of distal shell 86 is of 1.5 mm; the inner diameter of the distal shell 86 is identical to the outer diameter of tensioning ring and is 1.35 mm (for a jacket having an outer diameter of 1.5 mm and a wall thickness of 0.075 mm); and the inner diameter of the tensioning ring is 1.2 mm. According to an embodiment of this presentation, distal shell 86 and tensioning ring 76 can be formed out of two sections of metal tube attached together, or they can be lathed out of a single metal piece together. According to the embodiment illustrated in FIG. 11, the longitudinal recesses 80 are cut along the full length of the wall of the tensioning ring 76 from the proximal end to distal end of tensioning ring 76.

Figure 12:
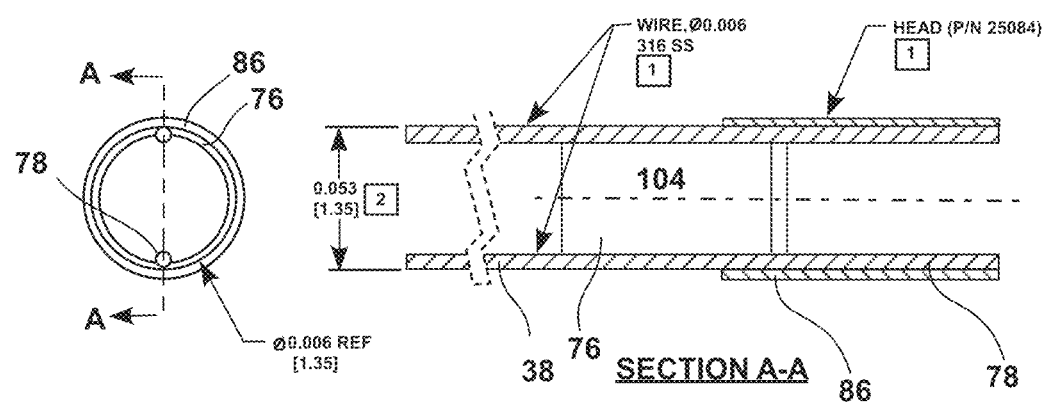
FIG. 12 comprises front and cross-section views of a distal shell attached to a tensioning ring as shown in FIG. 11 and to tensioning wires according to an embodiment of this presentation.

FIG. 12 comprises, from left to right, a front view and a longitudinal cross-section of distal shell 86 attached to a tensioning ring 76 and to the distal ends 78 of the tensioning wires 38; showing exemplary sizes according to an embodiment of this presentation where the outer diameter of tensioning ring is 1.35 mm and the diameter of the tensioning wire is 0.15 mm. Because the longitudinal recesses 80 are cut along the full length of the wall of the tensioning ring 76, the distal ends 78 of the tensioning wires 38 can be welded along the full length of the distal shell 86 and along the full length of the tensioning ring 76.

Figure 13:
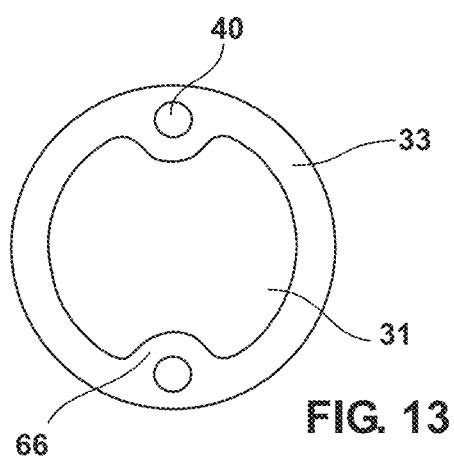
FIG. 13 shows an axial cross section of an elongated member such as illustrated in FIGS. 3 and 4.

FIG. 13 shows an axial cross section of the elongated member 33 such as illustrated in FIGS. 3 and 4, having a central lumen 31 and lateral longitudinal tensioning lumens 40 for passing the tensioning wire (not shown). According to an embodiment of this presentation, the central lumen 31 can have a narrower cross section in the vicinity 66 of the longitudinal tensioning lumens 40.

Figure 14:
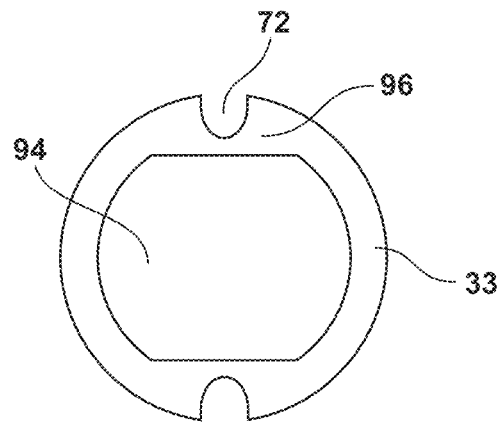
FIG. 14 shows an axial cross section of the elongated member such as illustrated in FIGS. 5 and 6.

FIG. 14 shows an axial cross section of the elongated member 33 such as illustrated in FIGS. 5 and 6, having a central lumen 94 and grooves 72 for passing the tensioning wire (not shown). According to an embodiment of this presentation, the central lumen 94 can have a narrower cross section in the vicinity 96 of the longitudinal tensioning lumens/grooves 72.

Figure 15A:
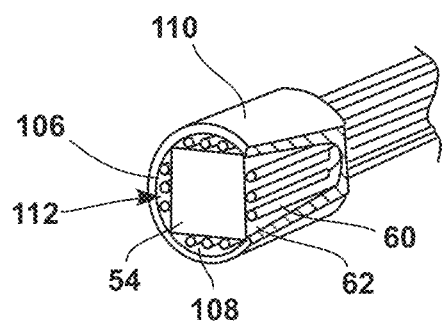
FIGS. 15A and 15B illustrate a process of attaching the distal ends of optical fibers to an imaging sensor according to an embodiment of this presentation.
Figure 15B:
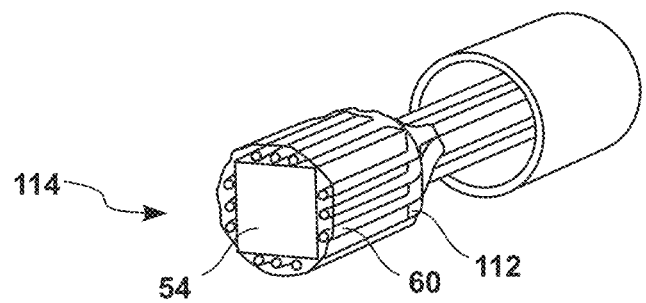

FIGS. 15A and 15B illustrate a process of attaching the distal ends of optical fibers 60 to an imaging sensor 54 having a rectangular (or square, as illustrated) cross section. The process comprises arranging said distal ends of the optic fibers 60 in a space 106 comprised between the walls 62 of the imaging sensor 54 and the inner walls 108 of a mounting tube 110 having an inner diameter equal to said diagonal of said rectangular cross section as shown in FIG. 12A; attaching permanently said distal ends of the optic fibers 60 to the imaging sensor 54, for example by introducing a glue or resin 112 in the spaces remaining between the fibers; and removing said mounting tube 110 as shown in FIG. 12A after the glue or resin 112 has set.

According to an embodiment of this presentation, the distal ends of the optic fibers 60 can be polished, together with a distal end (for example comprising an optical window) of the imaging sensor 54 after they are attached to the imaging sensor 54, such that light can be output by the polished ends of the optical fibers 60.

The assembly 114 of the imaging sensor 54, optical fibers 60 and resin 112 can then be arranged at the end of a tensioning ring 44 and an elongated member 33 as shown in FIG. 3, wherein the proximal extremities of the optical fibers—as well as an imaging cable attached to the proximal portion of the imaging sensor 54—are passed through central lumens of the tensioning ring 44 and elongated member 33, before sheathing the assembly 114, the tensioning ring 44 and elongated member 33 in a jacket 58 as illustrated in FIG. 3.

According to an embodiment of this presentation, the jacket 58 has an inner diameter equal to (or slightly larger than) the outer diameter of the assembly 114, the tensioning ring 44 and elongated member 33. A sheathing of elements having a given outer diameter into a jacket having an identical (or slightly larger) inner diameter is for example detailed in of PCT application No. PCT/US2015/027170, filed on Apr. 22, 2015 and entitled "STEERABLE MICRO-ENDOSCOPE", and is hereby incorporated by reference.

Figure 16A:
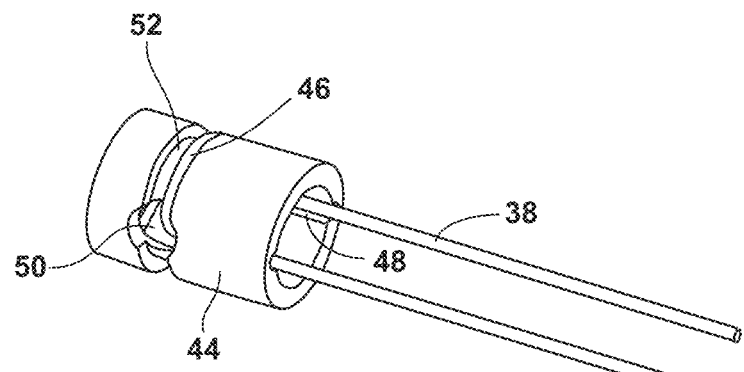
FIG. 16A is an elevation view of the tubular tensioning ring shown for example in FIGS. 3 and 4.

FIG. 16A is an elevation view of the tubular tensioning ring 44 shown for example in FIGS. 3 and 4, having two longitudinal recesses 48 cut in an inner wall of the tensioning ring and aligned with the longitudinal tensioning lumens 40 (not shown) of the elongated member 33 (not shown). The tubular tensioning ring 44 further comprises two axial recesses 50 (one shown) joining the longitudinal recesses 48 to a circumferential outer trench 52 cut in an outer wall of the tensioning ring 44. Two tensioning wires 38 have their distal end passing in the longitudinal recesses 48, then the radial recesses 50 and circumferential outer trench 52 to join in trench 52. According to an embodiment of this presentation, a single tensioning wire 38 can be bent in two, the bend of the wire being arranged in trench 52 and the ends of the wire being passed in radial recesses 50, then longitudinal recesses 48, then the longitudinal tensioning lumens 40 (not shown) of the elongated member 33 (not shown).

Figure 16B:
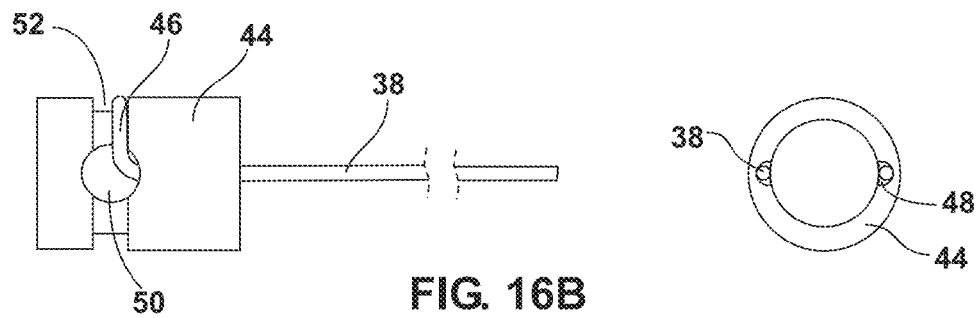
FIG. 16B comprises a side view and a cross-section of the tubular tensioning ring of FIG. 16A.

FIG. 16B comprises, from left to right, a side view and a cross-section of the tubular tensioning ring 44 shown for example in FIG. 16A.

Figure 17:
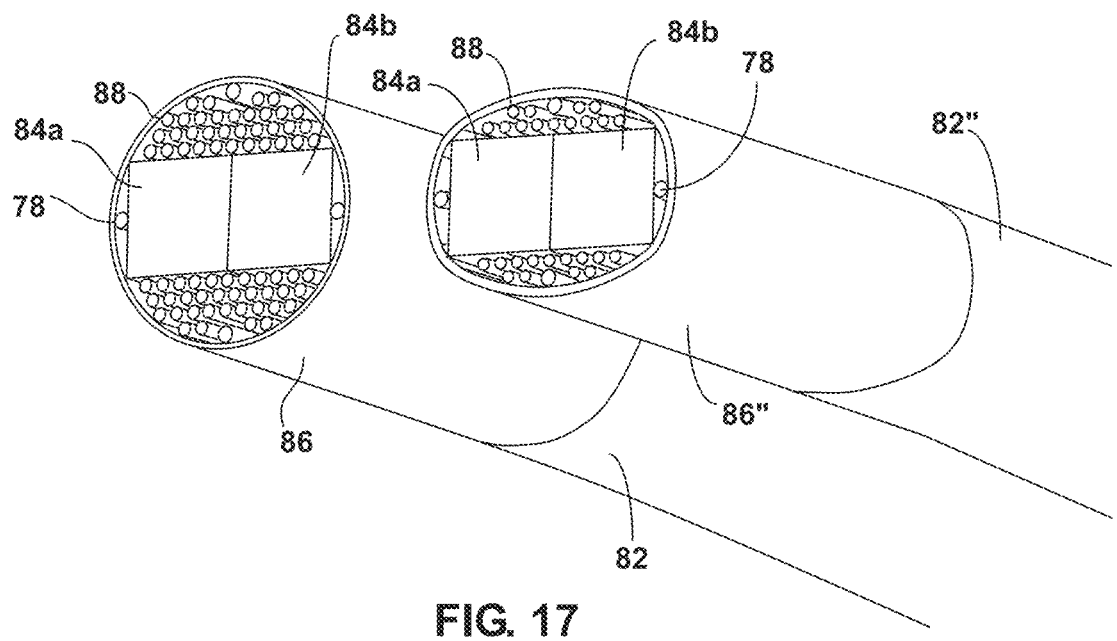
FIG. 17 comprises elevations view of the distal portion of the sheathed elongated member of two endoscopes according to an embodiment of this presentation.

FIG. 17 comprises, in its left part, an elevation view of the distal portion of the sheathed elongated member of an endoscope according to an embodiment of this presentation using a distal shell 86 as detailed in relation with FIGS. 5, 6, 11 and 12, where the longitudinal recesses (not shown) are cut along the full length of the wall of the tensioning ring (not shown) and the distal ends 78 of the tensioning wires 38 extend up to the distal end of distal shell 86 and can be welded along the full length of the distal shell 86. The embodiment shown in FIG. 17 comprises four tensioning wires arranged symmetrically along two perpendicular planes crossing at the longitudinal axis of the elongated member. Another embodiment can comprise a different number of tensioning wires, for example two tensioning wires arranged symmetrically along a plane containing the longitudinal axis of the elongated member, where said plane can be parallel to two lateral walls of the imaging sensor 84.

According to an embodiment of this presentation, the imaging sensor 84 having a rectangular cross section comprises two juxtaposed imaging sensors 84a, 84b of same cross-section; for example for generating stereo images. In the embodiment illustrated in FIG. 17, optical fibers 88 are shown arranged only along the two larger sides of the imaging sensor 84, but the optical fibers can as well be arranged along all the sides of the imaging sensor, depending on the space available between the sides of the imaging sensor and the inner wall of distal shell 86.

FIG. 17 comprises, in its right part, an elevation view of the distal portion of the sheathed elongated member of an endoscope according to another embodiment of this presentation, similar to the embodiment illustrated in the left part of FIG. 17, but having a distal shell 86 that has a non-circular cross section. According to this presentation, the elongated member and the distal shell have a same longitudinal axis and have a same, non-circular, cross section, where the inner walls of the distal shell 86 are arranged to circumscribe the longitudinal edges of the imaging sensor.

According to an embodiment of this presentation, the imaging sensor 84 can also have a non-rectangular cross section (not shown); the inner walls of the distal shell 86 being arranged to circumscribe the longitudinal edges of the imaging sensor.

Figure 18:
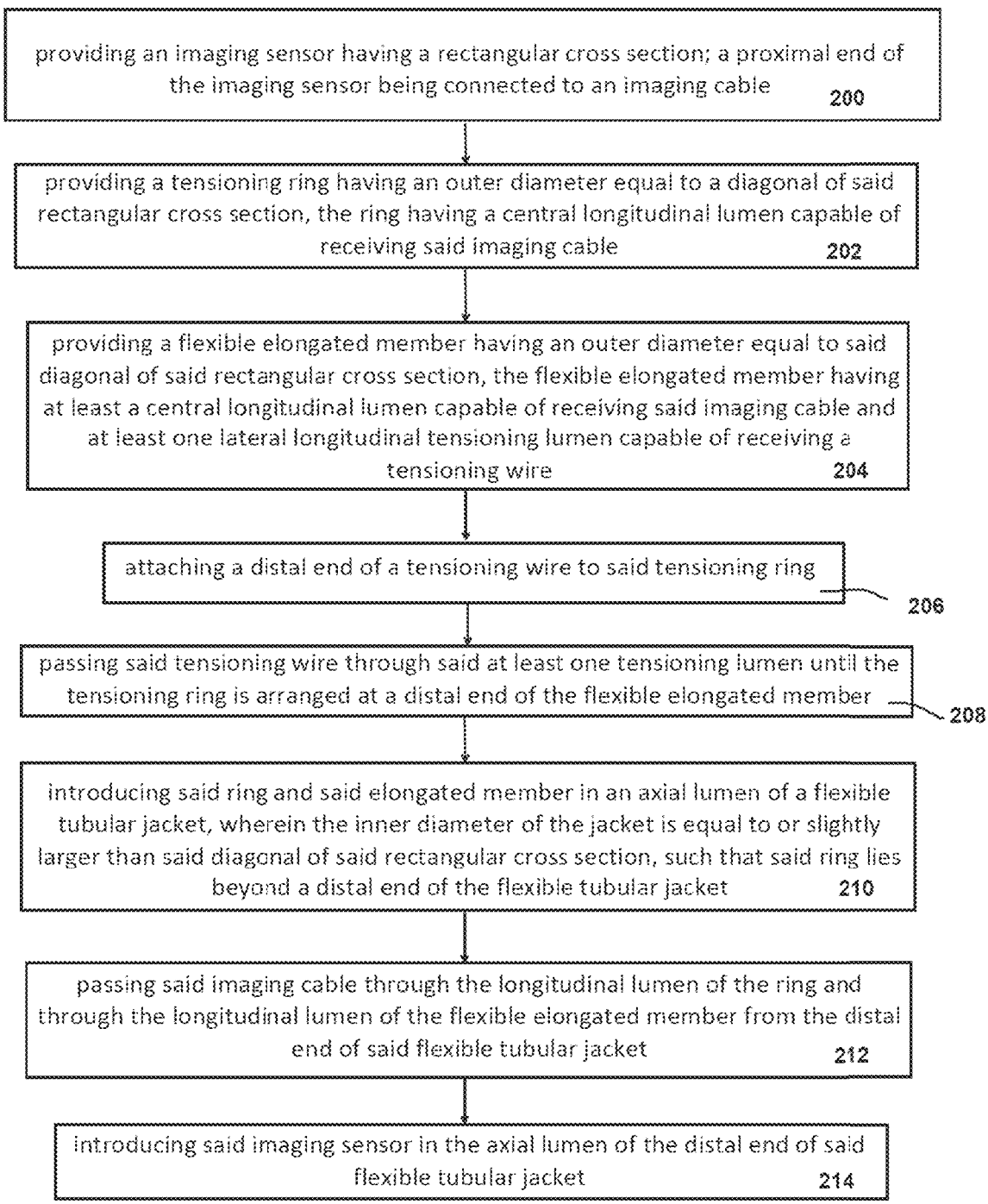
FIG. 18 is an organigram describing a method of making an endoscope such as illustrated in FIG. 3.

FIG. 18 is an organigram describing a method of making an endoscope according to this presentation, such as illustrated in FIG. 3; the method, comprising:

providing 200 an imaging sensor having a rectangular cross section; a proximal end of the imaging sensor being connected to an imaging cable;

providing 202 a tensioning ring having an outer diameter equal to a diagonal of said rectangular cross section, the ring having a central longitudinal lumen capable of receiving said imaging cable;

providing 204 a flexible elongated member having an outer diameter equal to said diagonal of said rectangular cross section, the flexible elongated member having at least a central longitudinal lumen capable of receiving said imaging cable and at least one lateral longitudinal tensioning lumen capable of receiving a tensioning wire;

attaching 206 a distal end of a tensioning wire to said tensioning ring;

passing 208 said tensioning wire through said at least one tensioning lumen until the tensioning ring is arranged at a distal end of the flexible elongated member;

introducing 210 said ring and said elongated member in an axial lumen of a flexible tubular jacket, wherein the inner diameter of the jacket is equal to or slightly larger than said diagonal of said rectangular cross section, such that said ring lies beyond a distal end of the flexible tubular jacket;

passing 212 said imaging cable through the longitudinal lumen of the ring and through the longitudinal lumen of the flexible elongated member from the distal end of said flexible tubular jacket;

introducing 214 said imaging sensor in the axial lumen of the distal end of said flexible tubular jacket.

FIG. 19 is an organigram describing possible further steps of the method illustrated in FIG. 18, comprising:

passing 216 the proximal ends of a plurality of optic fibers through a space comprised between the walls of the imaging sensor and the inner walls of said flexible tubular jacket, then through the longitudinal lumen of the ring and the elongated member;

arranging 218 distal ends of said plurality of optic fibers extending longitudinally along the imaging sensor in said space;

attaching permanently 220 the distal ends of said plurality of optic fibers in said space; and eventually polishing 222 said distal ends of a plurality of optic fibers attached to the imaging sensor, together with a distal end optical window of the imaging sensor.

FIG. 20 is an organigram describing a method of making an endoscope according to this presentation, such as illustrated in FIG. 5; the method, comprising:

providing 224 an imaging sensor having a rectangular cross section, a proximal end of the imaging sensor being connected to an imaging cable;

providing 226 a tubular shell having an inner diameter equal to a diagonal of said rectangular cross section; a proximal end of the tubular shell being attached to a distal end of a tensioning ring, the tensioning ring having an outer diameter smaller than an outer diameter of the tubular shell and having a central longitudinal lumen capable of receiving said imaging cable;

providing 228 a flexible elongated member having an outer diameter equal to the outer diameter of the tensioning ring, the flexible elongated member having at least a central longitudinal lumen capable of receiving said imaging cable and at least one lateral longitudinal tensioning lumen capable of receiving a tensioning wire;

attaching 230 a distal end of a tensioning wire to said tensioning ring;

passing 232 said tensioning wire through said at least one tensioning lumen;

introducing 234 said ring and said elongated member in an axial lumen of a flexible tubular jacket, wherein the inner diameter of the jacket is equal to or slightly larger than the outer diameter of the ring and elongated member;

passing 236 said imaging cable through the longitudinal lumen of the tensioning ring and of the flexible elongated member; and introducing 238 said imaging sensor in the tubular shell.

FIG. 21 is an organigram describing possible further steps of the method illustrated in FIG. 20, comprising:

passing 240 the proximal ends of a plurality of optic fibers through a space comprised between the walls of the imaging sensor and the inner walls of the tubular shell, then through the longitudinal lumen of the ring and the elongated member;

arranging 242 the distal ends of said plurality of optic fibers longitudinally along the imaging sensor in said space;

attaching 244 permanently said distal ends of a plurality of optic fibers in said space; and eventually polishing 246 said distal ends of a plurality of optic fibers attached to the imaging sensor, together with a distal end optical window of the imaging sensor.

Figure 22:
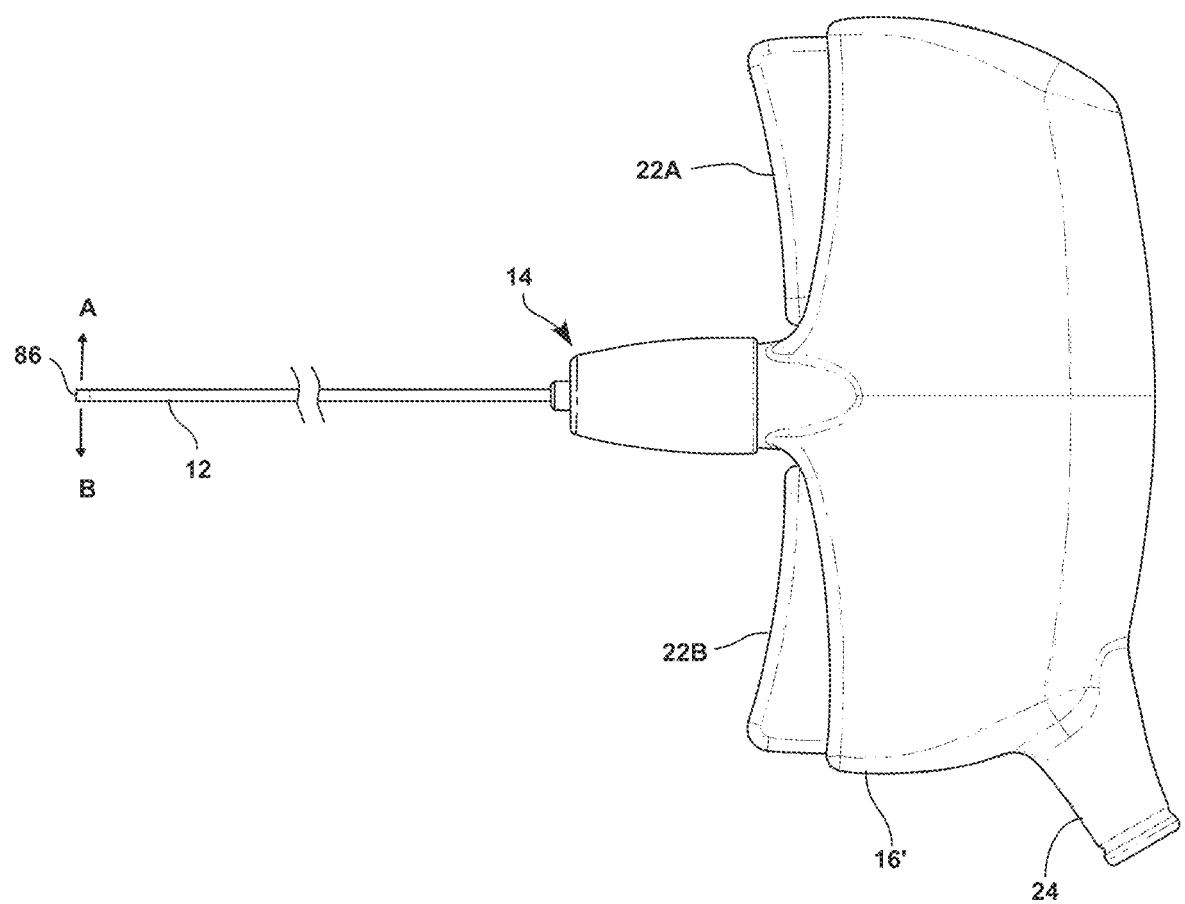
FIG. 22 is an elevation view of a steerable micro-device or endoscope according to an embodiment of this presentation.

FIG. 22 is an elevation view of a steerable micro-device or endoscope 300 according to an embodiment of this presentation, comprising a cylindrical elongated member 12 such as described for example in relation with any of FIG. 3 to 6 or 17, having a distal end and a proximal end 14, the elongated member 12 comprising at least a first lumen and a second lumen (such as lumens 40 of FIG. 3 or lumens/groove 72 of FIG. 5), a first tensioning wire running in the first lumen and a second tensioning wire running in the second lumen, the distal ends of the tensioning wires being attached at the distal end of the elongated member 12 (for example to a tensioning ring attached to a distal shell 86) and the proximal ends of the tensioning wires exiting the lumens at the proximal end 14 of the elongated member 12.

According to an embodiment of this presentation, the elongated member 12 and the first and second lumens are arranged such that the distal portion of the elongated member 12 bends in a first direction (A) when the proximal end of the first tensioning wire is pulled and in a second direction (B) when the proximal end of the second tensioning wire is pulled. According to an embodiment of this presentation the proximal end 14 of the elongated member 12 is coupled to a handle 16', the handle 16' and the elongated member 12 forming a T-shaped arrangement wherein the leg of the T is the elongated member 12 and the head of the T is the handle 16'.

According to an embodiment of this presentation the handle 16' comprises a lever 22A, 22B arranged such that: compressing a first portion 22A of the handle, located on one side (above the T leg in FIG. 22) of the proximal end 14 of the elongated member 12, pulls the first tensioning wire; and compressing a second portion 22B of the handle 16', located on the other side (below the T leg in FIG. 22) of the proximal end 14 of the elongated member 12, pulls the second tensioning wire. According to an embodiment of this presentation, the T-shaped handle 16' can comprise a connector 24 for connecting a cable that allows powering the endoscope and/or binging light to the optical fibers and receiving video imaging signals from imaging able attached to the imaging sensor in the distal shell 86.

Figure 23:
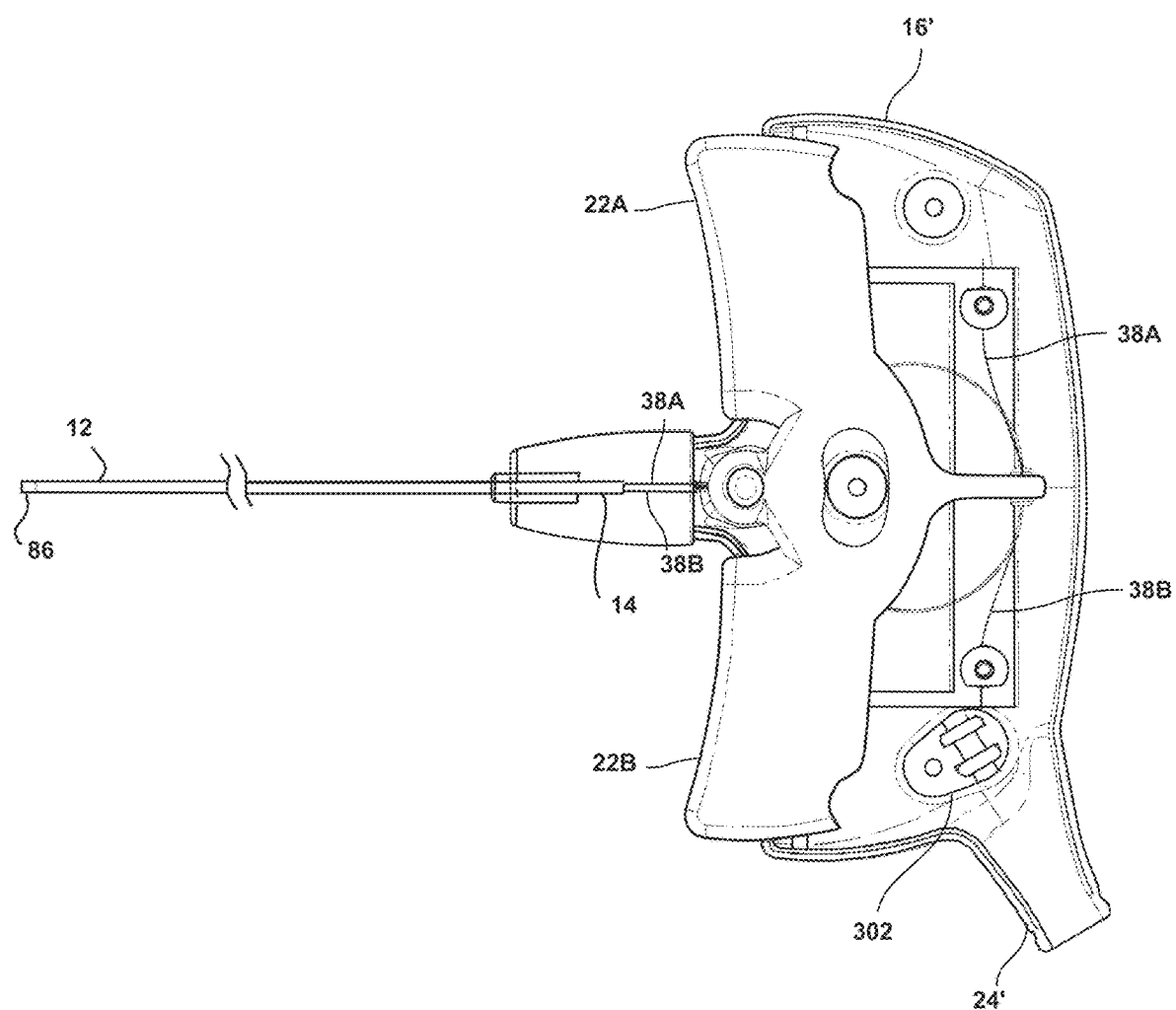
FIG. 23 is a partly opened view of a steerable micro-device or endoscope as shown in FIG. 22.

FIG. 23 is a partly open view of a steerable micro-device or endoscope as shown in FIG. 22. According to an embodiment of this presentation, the handle 16' is sized and shaped such that: the handle 16' can be held in the clutched hand of a user, with the proximal end 14 of the elongated member 12 passing between two fingers of said hand of a user (for example the major and annular of the hand).

According to an embodiment of this presentation, the handle 16' is sized and shaped such that tightening the grip on the handle 16' with the side of the hand closer to the index compresses the first portion 22A of the handle; and tightening the grip on the handle 16' with the side of the hand closer to the auricular compresses the second portion 22B of the handle.

FIG. 23 shows that the proximal ends of the two tensioning wires 38A, 38B that are respectively pulled when compressing the two portions of the lever, 22 A and 22B.

According to an embodiment of this presentation, illustrated in FIG. 23, housing 16' can, alternatively to comprising a connector 24, comprise a port 24' arranged for passing the imaging cable from the imaging sensor in the distal shell 86 and the optical fibers the distal end of which are attached in the distal shell 86. According to an embodiment of this presentation, a screw wise 302 can be provided for holding the cable and optical fibers in the housing 16'.

A device according to this presentation, having a camera and an optic fiber to transmit light, is particularly suitable as a micro-endoscope in the medical domain, but it can also be used in the automotive domain or the home improvement domain to look into hard-to-reach locations.

The Applicant has made this disclosure with respect to the current state of the art, but also contemplates advancements and that adaptations in the future may take into consideration of those advancements, namely in accordance with the then current state of the art. It is intended that the scope of the invention be defined by the Claims as written and equivalents as applicable. Reference to a claim element in the singular is not intended to mean "one and only one" unless explicitly so stated. Moreover, no element, component, nor method or process step in this disclosure is intended to be dedicated to the public regardless of whether the element, component, or step is explicitly recited in the Claims. No claim element herein is to be construed under the provisions of 35 U.S.C. Sec. 112, sixth paragraph, unless the element is expressly recited using the phrase "means for . . . " and no method or process step herein is to be construed under those provisions unless the step, or steps, are expressly recited using the phrase "comprising the step(s) of . . . ."

The invention claimed is:

1. An endoscope comprising:
   a tubular elongated member having a longitudinal axis, a proximal end and a distal end;
   at least one tensioning wire arranged in a tensioning lumen along one side of the elongated member, between the proximal end and the distal end of the elongated member;
   a head arranged at the distal end of the elongated member, the head comprising:
   a tubular tensioning ring attached to the distal end of the tensioning wire, the tensioning ring having a same external diameter as the elongated member;
   an imaging sensor having a rectangular cross section, arranged at a distal end of the head; and
   a tubular distal shell arranged longitudinally around the imaging sensor, the distal shell having an inner diameter identical to or larger by up to 10 microns than a diagonal of the rectangular cross section of the imaging sensor;
   wherein a tubular jacket sheathes the elongated member and the tensioning ring of the head;
   wherein the distal shell has a proximal end that is attached to a distal end of the tensioning ring; the proximal end of the tensioning ring being abutted to the distal end of the elongated member; and
   wherein the tensioning ring comprises a longitudinal cut extending from a proximal end of the tensioning ring; the distal end of the tensioning wire extending along and being welded into the longitudinal cut such that the tensioning wire does not extend radially beyond the external diameter of the tensioning ring.

2. The endoscope of claim 1, wherein the distal shell of the head has an outer diameter identical to the outer diameter of the tubular jacket.

3. The endoscope of claim 1, wherein a distal end of a plurality of optical fibers is arranged between the inner diameter of the distal shell and lateral walls of the imaging sensor; the optical fibers passing through a lumen in the tensioning ring and a lumen in the elongated member.

4. The endoscope of claim 1 wherein the elongated member comprises two tensioning lumens and two tensioning wires, arranged symmetrically with respect to the longitudinal axis of the elongated member.

5. An endoscope comprising:
   a tubular elongated member having a longitudinal axis, a proximal end and a distal end;
   at least one tensioning wire arranged in a tensioning lumen along one side of the elongated member, between the proximal end and the distal end of the elongated member;
   a head arranged at the distal end of the elongated member, the head comprising:
   a tubular tensioning ring attached to the distal end of the tensioning wire, the tensioning ring having a same external diameter as the elongated member;
   an imaging sensor having a rectangular cross section, arranged at a distal end of the head; and
   a tubular distal shell arranged longitudinally around the imaging sensor, the distal shell having an inner diameter identical to or larger by up to 10 microns than a diagonal of the rectangular cross section of the imaging sensor;
   wherein a tubular jacket sheathes the elongated member and the tensioning ring of the head;
   wherein the distal shell has a proximal end that is attached to a distal end of the tensioning ring; the proximal end of the tensioning ring being abutted to the distal end of the elongated member; and
   wherein the tensioning lumen of the elongated member is a longitudinal groove cut in the outer surface of the elongated member; the tensioning wire being retained in the groove by the tubular sheath.

6. The endoscope of claim 5, wherein the elongated member comprises a central lumen; the central lumen having a narrower cross section opposite the longitudinal groove in the outer surface of the elongated member.

7. An endoscope comprising:
   a tubular elongated member having a longitudinal axis, a proximal end and a distal end;
   at least one tensioning wire arranged in a tensioning lumen along one side of the elongated member, between the proximal end and the distal end of the elongated member;
   a head arranged at the distal end of the elongated member, the head comprising:
   a tubular tensioning ring attached to the distal end of the tensioning wire, the tensioning ring having a same external diameter as the elongated member;
   an imaging sensor having a rectangular cross section, arranged at a distal end of the head; and
   a tubular distal shell arranged longitudinally around the imaging sensor, the distal shell having an inner diameter identical to or larger by up to 10 microns than a diagonal of the rectangular cross section of the imaging sensor;
   wherein a tubular jacket sheathes the elongated member and the tensioning ring of the head;

wherein the distal shell is formed by the distal end of the tubular jacket; the tubular jacket sheathing the elongated member, the tensioning ring and the imaging sensor of the head; the proximal end of the tensioning ring being abutted to the distal end of the elongated member;

wherein the elongated member comprises two longitudinal tensioning lumens and two tensioning wires, arranged symmetrically with respect to the longitudinal axis of the elongated member; and wherein the tensioning ring comprises:

two longitudinal recesses cut in an inner wall of the tensioning ring, and aligned with the longitudinal tensioning lumens of the elongated member, and two radial recesses joining the longitudinal recesses to a circumferential outer trench cut in an outer wall of the tensioning ring;

the distal ends of the two tensioning wires being arranged in said two longitudinal recesses and said two radial recesses, and being joined in said circumferential outer trench.

8. The endoscope of claim 7, wherein the longitudinal tensioning lumens of the tubular elongated member are formed in the thickness of the elongated member.

9. The endoscope of claim 8, wherein the elongated member comprises a central lumen; the central lumen having a narrower cross section near the longitudinal tensioning lumens.

* * * * *